US012589088B2

(12) United States Patent
Banerjee et al.

(10) Patent No.: US 12,589,088 B2
(45) Date of Patent: Mar. 31, 2026

(54) COMPOSITIONS AND METHODS FOR TREATING CANCER WITH ANDROGRAPHOLIDE AND MELATONIN COMBINATION THERAPY

(71) Applicants: University of Maryland, Baltimore, Baltimore, MD (US); GlycoMantra, Inc., Baltimore, MD (US)

(72) Inventors: Aditi Banerjee, Catonsville, MD (US); Steven Czinn, Pikesville, MD (US); Hafiz Ahmed, Leesburg, VA (US); Thomas Blanchard, Baltimore, MD (US)

(73) Assignees: UNIVERSITY OF MARYLAND, BALTIMORE, Baltimore, MD (US); GLYCOMANTRA INC., Baltimore, MD (US)

( * ) Notice: Subject to any disclaimer, the term of this patent is extended or adjusted under 35 U.S.C. 154(b) by 604 days.

(21) Appl. No.: 17/921,803

(22) PCT Filed: Apr. 30, 2021

(86) PCT No.: PCT/US2021/030084

§ 371 (c)(1),
(2) Date: Oct. 27, 2022

(87) PCT Pub. No.: WO2021/222700

PCT Pub. Date: Nov. 4, 2021

(65) Prior Publication Data

US 2023/0165832 A1 Jun. 1, 2023

Related U.S. Application Data

(60) Provisional application No. 63/018,330, filed on Apr. 30, 2020.

(51) Int. Cl.
*A61K 31/365* (2006.01)
*A61K 31/4045* (2006.01)
*A61P 1/00* (2006.01)
*A61P 35/00* (2006.01)
*A61P 35/04* (2006.01)

(52) U.S. Cl.
CPC ........ *A61K 31/365* (2013.01); *A61K 31/4045* (2013.01); *A61P 1/00* (2018.01); *A61P 35/00* (2018.01); *A61P 35/04* (2018.01)

(58) Field of Classification Search
CPC ................................................... A61K 31/365
See application file for complete search history.

(56) References Cited

U.S. PATENT DOCUMENTS

2019/0275119 A1 9/2019 Howes

OTHER PUBLICATIONS

Jiang et al. Anticancer Research, 2007, 27(4B) 2439-2447.*
Leon et al. Journal of Pineal Research, 2014, 56(4): 415-426.*
International Search Report from Appl. No. PCT/US21/30084, mailed on Sep. 9, 2021.
Sharda et al., Impact of Andrographolide and Melatonin Combinatorial Drug Therapy on Metastatic Colon Cancer Cells and Organoids. Clinical Medicine Insights: Oncology, (2021), 15:1-9.
Islam et al., Andrographolide, a diterpene lactone from Andrographis paniculata and its therapeutic promises in cancer, Cancer Letter 420, (2018), 129-145.

* cited by examiner

*Primary Examiner* — Rei Tsang Shiao
(74) *Attorney, Agent, or Firm* — Nevrivy Patent Law Group P.L.L.C.

(57) ABSTRACT

The present invention provides methods for treating cancer in a subject, comprising administering to the subject an effective amount of a combination of andrographolide and melatonin. The present invention further provides compositions comprising effective amounts of andrographolide and melatonin for treating cancer.

22 Claims, 13 Drawing Sheets

Specification includes a Sequence Listing.

COMPOSITIONS AND METHODS FOR TREATING CANCER WITH ANDROGRAPHOLIDE AND MELATONIN COMBINATION THERAPY

CROSS-REFERENCE TO RELATED APPLICATIONS

This application claims the benefit of U.S. Provisional Appl. No. 63/018,330, filed Apr. 30, 2020, which is incorporated by reference herein.

INCORPORATION-BY-REFERENCE OF MATERIAL SUBMITTED ELECTRONICALLY

Incorporated by reference in its entirety herein is a computer-readable sequence listing submitted concurrently herewith and identified as follows: One 2,807 Byte ASCII (Text) file named "sequence_Listing_ST25.txt," created on Apr. 28, 2021.

FIELD OF THE INVENTION

The field of the invention generally relates to medicine and pharmaceuticals, in particular to methods of treating colorectal cancer.

BACKGROUND OF THE INVENTION

It is estimated there will be 2.2 million new colorectal cancer (CRC) cases and 1.1 million related deaths by 2030 (Arnold et al., Gut, 2017, 66 (4):683-691; American Cancer Society, Survival Rates for Colorectal Cancer, 2020). CRC is caused by colospheroids (CSCs) driven tumor recurrence, metastasis, and resistance (Kozovska et al., Biomed Pharmacother, (2014), 68(8):911-6; Munro et al., J Clin Pathol, (2018), 71(2):110-116; Wielenga et al., Cell, (2015), Rep 13(3):489-494). The American Cancer Society (ACS) estimates that, in 2021 alone, there will be 104,270 new diagnoses of colon cancer in the United States. While the majority of CRCs occur in adults ages 50 and older, 17,930 (12%) cases are diagnosed in individuals younger than age 50, the equivalent of 49 new cases per day. It's expected to cause about 52,980 deaths during 2021 (American Cancer Society, Survival Rates for Colorectal Cancer, (2020, 2021).

Chemotherapy, targeted therapy, and immunotherapy are the current treatment options for CRC, though each strategy has its own limitations (Chapuis et al., Colorectal Dis, (2019), 21(2):164-173; Dienstmann et al., J Clin Oncol, (2015), 33(16):1787-1796; Hodgkinson et al., Tumour Biol, (2017), 39(10):1010428317734691). Therefore, targeting mCRC cells via molecular targets remain important in colon cancer therapy. Conventional therapies target proliferating and differentiated cancer cells with limited cancer stem cell (CSC) killing (Baccelli et al., J Cell Biol, (2012) 198(3): 281-93).

Earlier studies have demonstrated that the plant metabolite andrographolide (AGP) induces CRC cell death due to apoptosis and is associated with the activation of IRE-1, an ER stress marker (Banerjee et al., Oncotarget, (2016), 7(27):41432-41444). Additional studies showed that AGP induces apoptotic cell death through the induction of reactive oxygen species (ROS) which eventually play a role in down-regulating cell cycle progression and cell survival pathways (Banerjee et al., Oncotarget, (2017), 8(16):26142-26153). AGP also induces cell death through the inhibition of angiogenic signaling, which is inversely related to the tumor suppressor gene expression, RASSF1A (Blanchard et al., Cell Physiol Biochem, (2018), 48(3):1259-1273). In the context of cancer, AGP can diminish resistance to 5-Fluorouracil (5-FU), a first-line chemotherapeutic agent for CRC patients (Islam et al., Cancer Lett, (2018), 420:129-145; Wang et al., Biochem Pharmacol, (2016), 121:8-17). Although 5-Fluorouracil (5-FU) is a useful chemotherapy treatment, 5-FU resistance is a major contributor for poor prognosis.

Recent studies have also shown that melatonin (MLT) has antimetastatic properties by modulating cell-cell and cell-matrix interactions, remodeling the extracellular matrix, and suppressing angiogenesis (Akbarzadeh et al., Sci Rep, (2017), 7(1):17062; Hao et al., J Exp Clin Cancer Res, (2019), 38(1):48; Su et al., J Pineal Res, (2017), 62(1)). In addition, extensive experimental data demonstrates that this chronobiotic agent exerts oncostatic effects throughout all stages of tumor growth, from initial cell transformation to mitigation of malignant progression and metastasis; additionally, MLT alleviates the side effects and improves the welfare of radio/chemotherapy-treated patients (Gil-Martin et al., Med Res Rev, (2019), 39(6):2239-2285). Moreover, it inhibits CRC proliferation by increasing reactive oxygen species (ROS) and inducing apoptosis, autophagy, and senescence (Buldak et al., Mol Med Rep, (2015), 12(2): 2275-2282). Additionally, MLT also causes drug-resistant CRC cell death and inhibits CRC-colospheroids when it is co-administered with 5-FU (Lee et al., J Pineal Res, (2018), 65(4):e12519).

Combination therapy, a treatment modality which combines two or more therapeutic agents, is a cornerstone of cancer therapy (Bayat et al., Oncotarget, (2017), 8(23): 38022-38043; Wang et al., Drug Des Devel Ther, (2018), 12:3171-3180). Combination therapy has been proposed to prevent and overcome drug resistance (Gayvert et al., PLoS Comput Biol, (2017), 13(1):e1005308; Gu et al., Curr Opin Pharmacol, (2016), 31:97-103; Riesco-Martinez et al., Cancer Lett, (2017) 400:311-318). Moreover, this therapy is a promising strategy for synergistic anticancer treatment. It has different mechanisms of action that could reduce the dose of each agent, thus may reduce the individual drug-related toxicity (Wang et al., Drug Des Devel Ther, (2018), 12:3171-3180). Drug association may lead to synergic protective effects at concentrations substantially lower than those used when given separately.

The mechanism of many drugs' actions remains unknown and the validity of the independence assumption is often not met (Gayvert et al., PLoS Comput Biol, (2017), 13(1): e1005308). Therefore, to investigate synergistic drug combinations, the drug Combination Index (CI) is utilized. The CI quantitatively depicts synergism (CI<1), additive effect (CI=1), and antagonism (CI>1) (Chou 2006, 2011a; Chou et al., 1994; Chou and Talalay 1984). Its applications have been expedited with the median-effect equation based on the "mass action law" (Chou, T. C., Integr Biol (Camb), (2011b), 3(5):548-59; Keith, C. T., A. A., Nat Rev Drug Discov, (2005), 4(1):71-8). An updated program of the Chou-Talalay theory, known as CompuSyn, was introduced in 2005 (Zhang et al., Am J Cancer Res, (2016), 6(1):97-104).

There is great potential for applying combination therapy to the problem of targeting CSCs and also great challenge and opportunity given the variety of possibly applicable drug combinations. There is a great need in the art for finding improved treatment methods for CRC, and this remains a formidable and important goal.

The foregoing description of the background is provided to aid in understanding the invention and is not admitted to be or to describe prior art to the invention.

SUMMARY OF THE INVENTION

It is to be understood that both the present general description of the invention and the following detailed description are exemplary, and thus do not restrict the scope of the invention.

As provided herein, AGP is shown to inhibit CRC cell growth with reduced concentration compared to prior studies when combined with the safe, anti-cancer compound MLT. It is demonstrated that this dual compound has an impact on a panel of metastatic CRC cells (T84, Colo 205, HCT-15, HT-29, and DLD-1), and requires a concentration 3 times less than in previous studies. Moreover, these combinatorial therapies exert a little impact on normal cells.

In one aspect, the present invention meets the above-described need with a combination therapy for the treatment of cancer, such as colorectal cancer, that includes andrographolide (AGP) and melatonin (MLT). The impact of co-treatment with AGP and MLT on metastatic CRC cells (T84, Colo 205, HCT-15, HT-29, and DLD-1), CSCs isolated from CRC cell lines (HT-29s and HCT-15-s) and on patient derived organoids (PDO) was examined. The present inventors demonstrate herein that AGP and MLT act together to suppress cell proliferation and stem cell spheroid formation (CSCs, HT-29-s and HCT-15-s) and to cause a loss of membrane integrity in patient derived organoids (Banerjee et al., Eur J Pharmacol, (2021), 897:173919; Sharda et al., DOI: 10.1177/11795549211012672/ID: ONC-20-0135, Clin. Med. Insights Oncol, (2021). The present inventors further show that the disruption of spheroid formation is due to inhibition of IRE-1, MLT receptor 1B (MT-2) and stem cell Nanog expression. (Spheroid formation is characteristic of some CSC lines.).

In another aspect, the invention provides a method of treating cancer in a subject, the method comprising administering to the subject an effective amount of a combination of andrographolide and melatonin.

In some embodiments, the combination of andrographolide and melatonin is synergistic.

In some embodiments, the subject can be a human subject.

In some embodiments, the cancer can be colorectal cancer.

In some embodiments, the cancer in the subject can comprise at least one solid tumor.

In certain embodiments, the solid tumor can be a sarcoma, a neuroblastoma, or a lymphoma.

In some embodiments, a dose of the combination of andrographolide (AGP) and melatonin (MLT) can comprise from about 500 mg to about 3000 mg of AGP and from about 1000 mg to about 6000 mg of MLT.

In some embodiments, a dose of the combination of andrographolide (AGP) and melatonin (MLT) can comprise from about 0.05 g to about 5 g of AGP and from about 0.25 g to about 10 g of MLT.

In some embodiments, a dose of the combination of andrographolide (AGP) and melatonin (MLT) can comprise from about 1 mg/kg body weight of the subject to about 20 mg/kg body weight of the subject of AGP and from about 10 mg/kg body weight of the subject to about 250 mg/kg body weight of the subject of MLT.

In some embodiments of the above method for treating cancer in a subject, a weight ratio of andrographolide to melatonin can be in a range of from about 1:1 to about 1:20.

In some embodiments of the above method for treating cancer in a subject, a weight ratio of andrographolide to melatonin is in a range of from about 1:10 to about 1:15.

In certain embodiments, a dose of the combination of andrographolide (AGP) and melatonin (MLT) can further comprise a pharmaceutically acceptable carrier.

In some embodiments, a dose of the combination of andrographolide and melatonin can be administered orally.

In some embodiments, a dose of the combination of andrographolide and melatonin can be in the form of a capsule, a tablet, a pill, a powder, a gel cap, or granules.

In some embodiments, a dose of the combination of andrographolide and melatonin can be in the form of a controlled release capsule, tablet, or pill.

In another aspect, the present invention provides a composition for treating cancer in a subject, the composition comprising a combination of andrographolide and melatonin.

In some embodiments, the cancer treated by the composition can be colorectal cancer.

In some embodiments, the subject in whom cancer is treated can be a human subject.

In some embodiments, the composition comprising a combination of andrographolide and melatonin can further comprise a pharmaceutically acceptable carrier.

In some embodiments of the composition of the present invention, a weight ratio of andrographolide to melatonin can be in a range of from about 1:1 to about 1:30.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The skilled artisan will understand that the drawings, described below, are for illustration purposes only. The drawings are not intended to limit the scope of the present teachings in any way.

Colospheroids (HT-29-s and HCT-15-s) were treated with the $IC_{50}$ dose of AGP and MLT at 48 h. A. Percentage of viable colospheroids were monitored using the MTT assay at indicated doses. B. Enumeration of colospheroids with altered morphology. At least 100 colospheroids per well were counted. C. Morphological alterations in HT29-s and HCT-15-s 48 h post treatment with AGP+MLT using phase contrast microscope. Magnification: 10×. D. Data shown are representative of five different fields. E. HT29-s were diluted and treated with AGP and MLT at indicated doses for 48 h. Growth was measured through direct counting of clonal clusters stained in multiwell plates with crystal violet. Representative photomicrographs are shown. F. quantification of number of colonies (P<0.01; *P<0.001).

Figure 4:
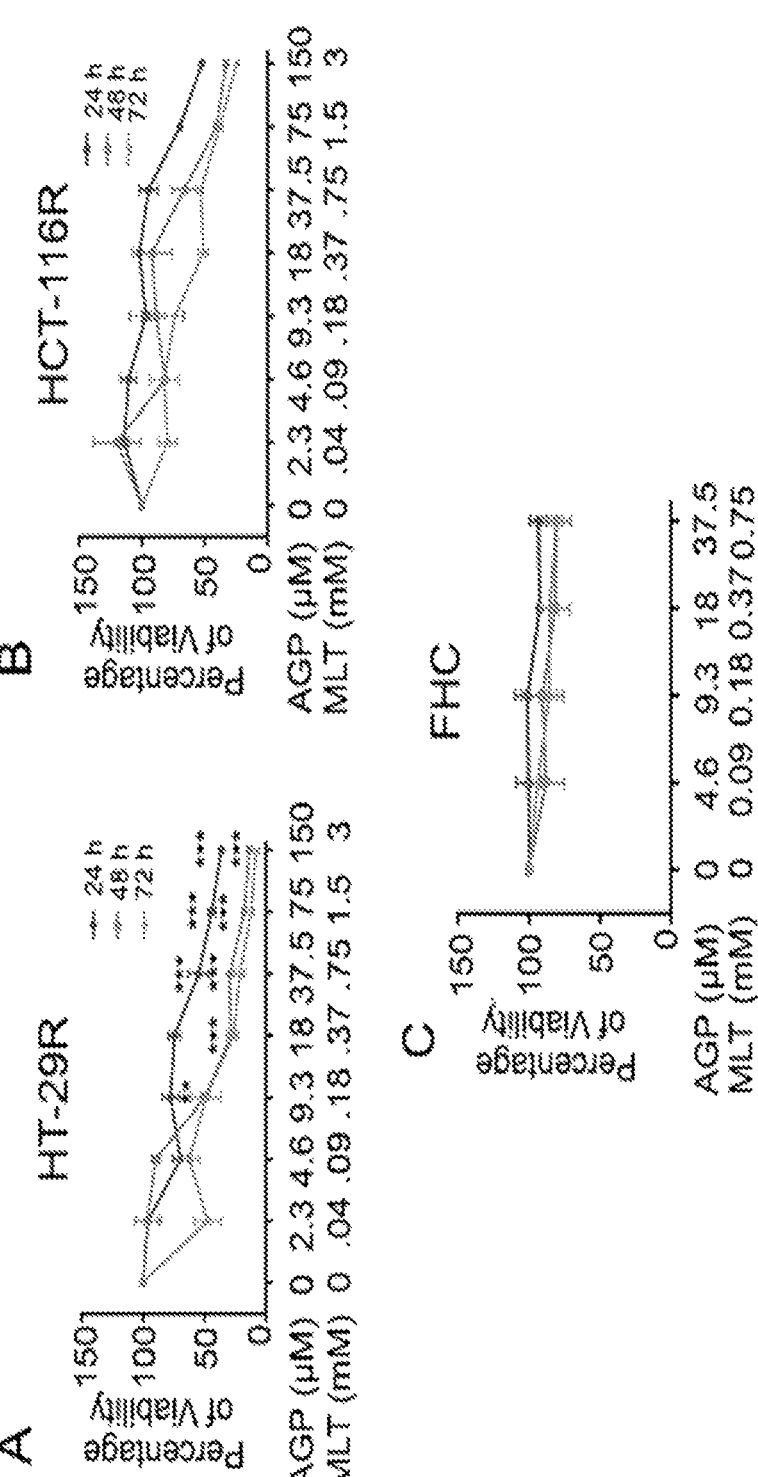

FIG. 4. AGP and MLT synergistically enhanced the anti-tumor effects of 5-FU on HT-29R and HCT-116R cells. A. HT-29R and B. HCT-116R cells were treated with the indicated concentrations of AGP (M) and MLT (mM) for 24, 48 and 72 h. Cell viability was quantified by MTT assay. C. Normal colon epithelial cells (FHC) were treated with the recommended complete medium containing a final concentration of 0.01% DMSO. The FHC cells were treated with different concentrations of AGP and MLT as indicated for 24, 48, and 72 h.

Figure 5:
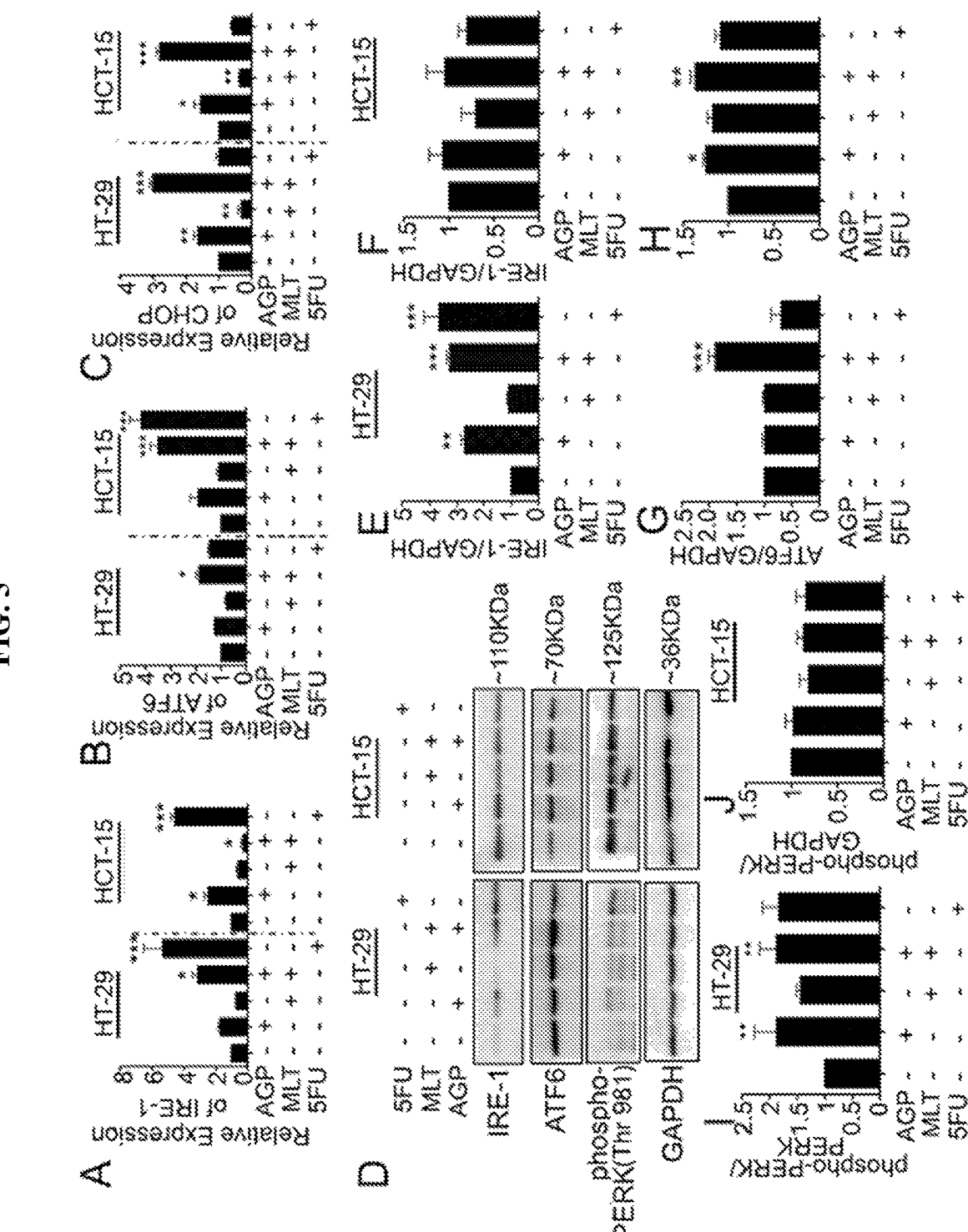

FIG. 5. AGP and MLT synergistically induce ER stress-related molecules. HT-29 and HCT-15 cells were treated with AGP, MLT, AGP+MLT, and 5-FU for 48 h as indicated in the methodology section. Transcriptional level of expression of ER stress associated genes was determined by qRT-PCR for A. IRE-1, B. ATF6, and C. CHOP. Bar graphs show quantitative results normalized to GAPDH mRNA levels. Results are from three independent experiments. D. Treated and untreated cells were lysed, and protein expression was determined by immunoblotting for IRE-1, ATF6, phospho-PERK, and GAPDH. Densitometry analysis was performed and normalized with GAPDH expression to demonstrate the expression of IRE-1 (E-F), ATF6 (G-H), and PERK (I-J) proteins.

Figure 6:
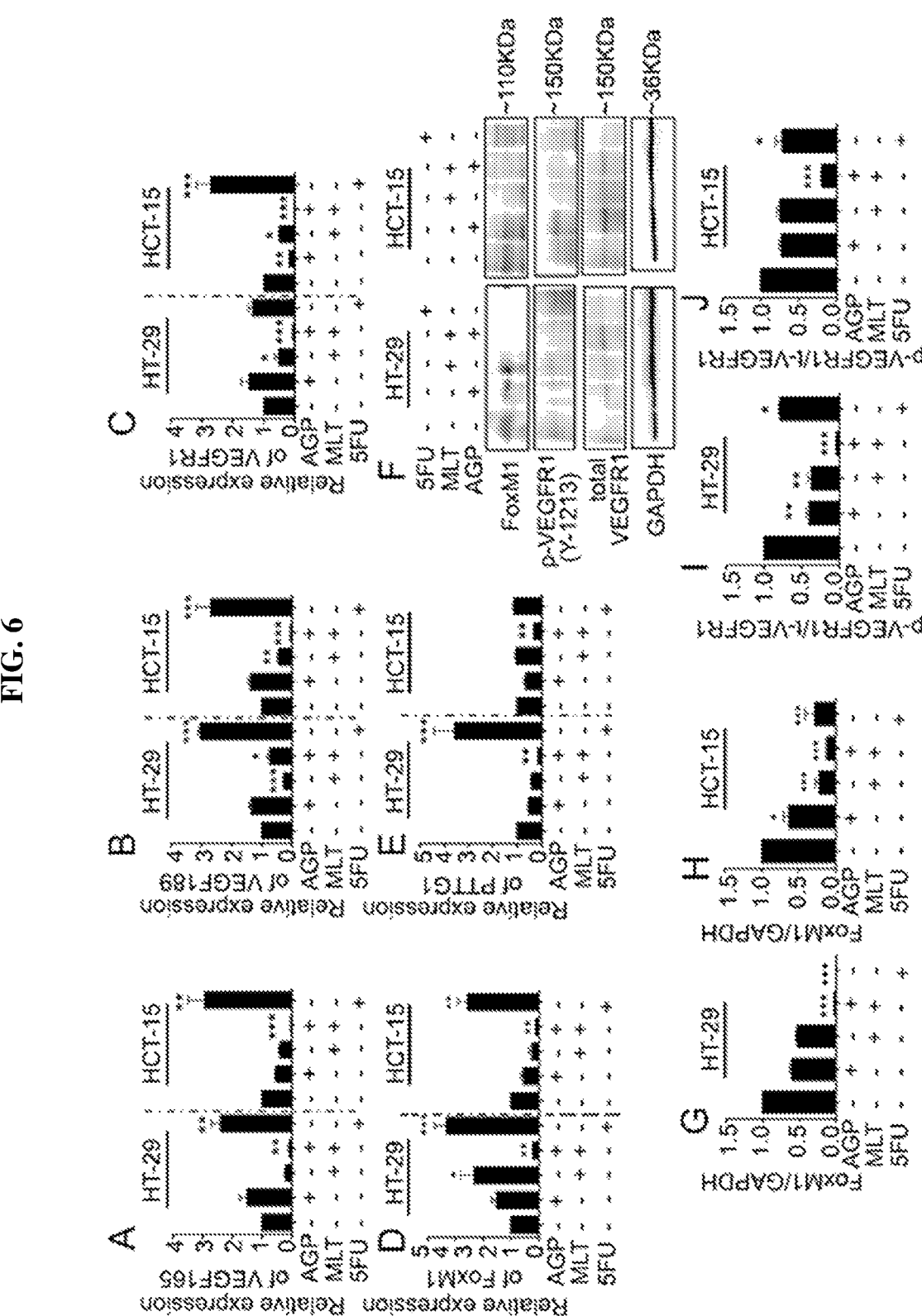

FIG. 6. AGP and MLT synergistically downregulates angiogenic signaling molecules in colon cancer cells. HT-29 (left) and HCT-15 (right) cells were analyzed for A. VEGF165, B. VEGF189, C. VEGF receptor1, D. FoxM1, E. PTTG1 mRNA expression in the presence and absence of AGP, MLT and 5-FU. F. HT-29 and HCT-15 cell lysates were subjected for protein expression as indicated. (G-H). Quantification of FoxM1 was normalized with GAPDH and (I-J). p-VEGF receptor1 was normalized with total VEGF receptor 1. Statistical significance was determined using one-way ANOVA followed Bonferroni test (*P<0.05, P<0.01, *P<0.001).

Figure 7:
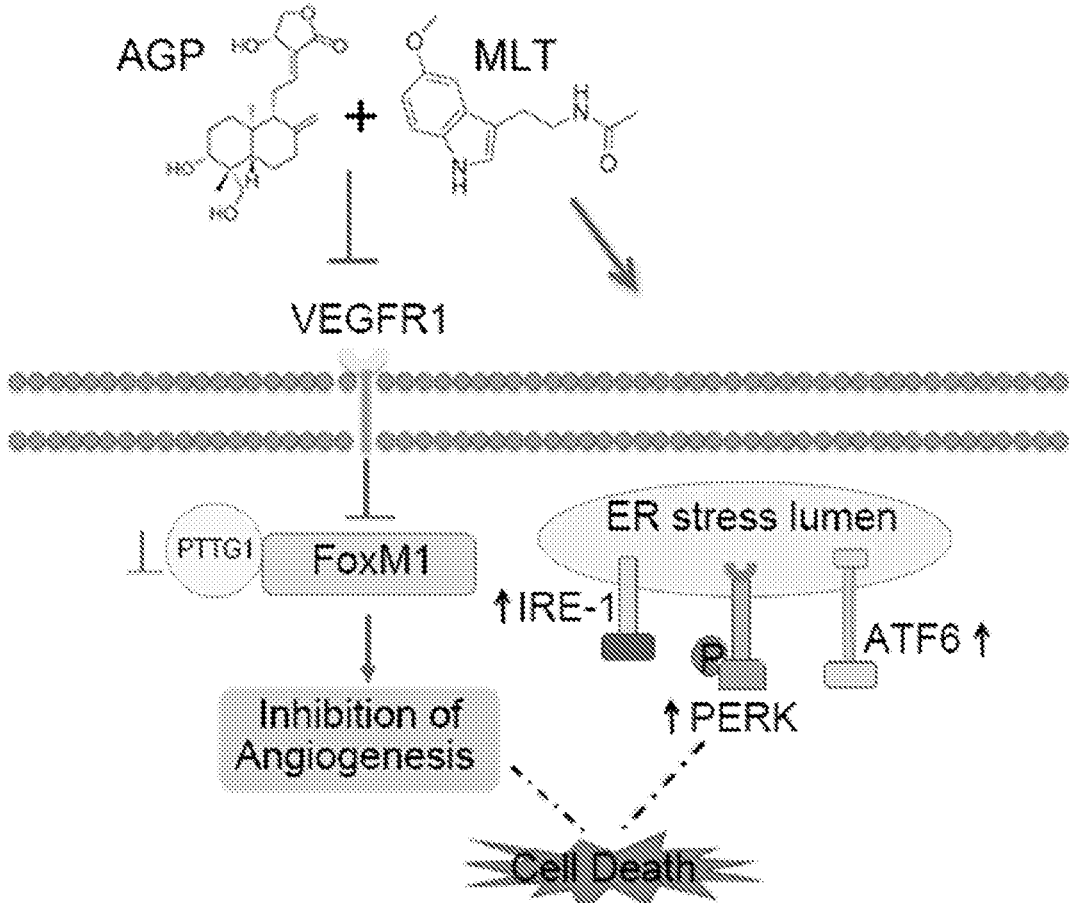

FIG. 7. Schematic representation of the modulation of the UPR arms and angiogenic signal by the synergistic impact of AGP and MLT on CRC cells. We illustrated that the combinatorial effect causes inhibition of angiogenic signal (downregulation of VEGF receptor1, FoxM1, and PTTG1) and upregulation of ER transducers.

Figure 8:
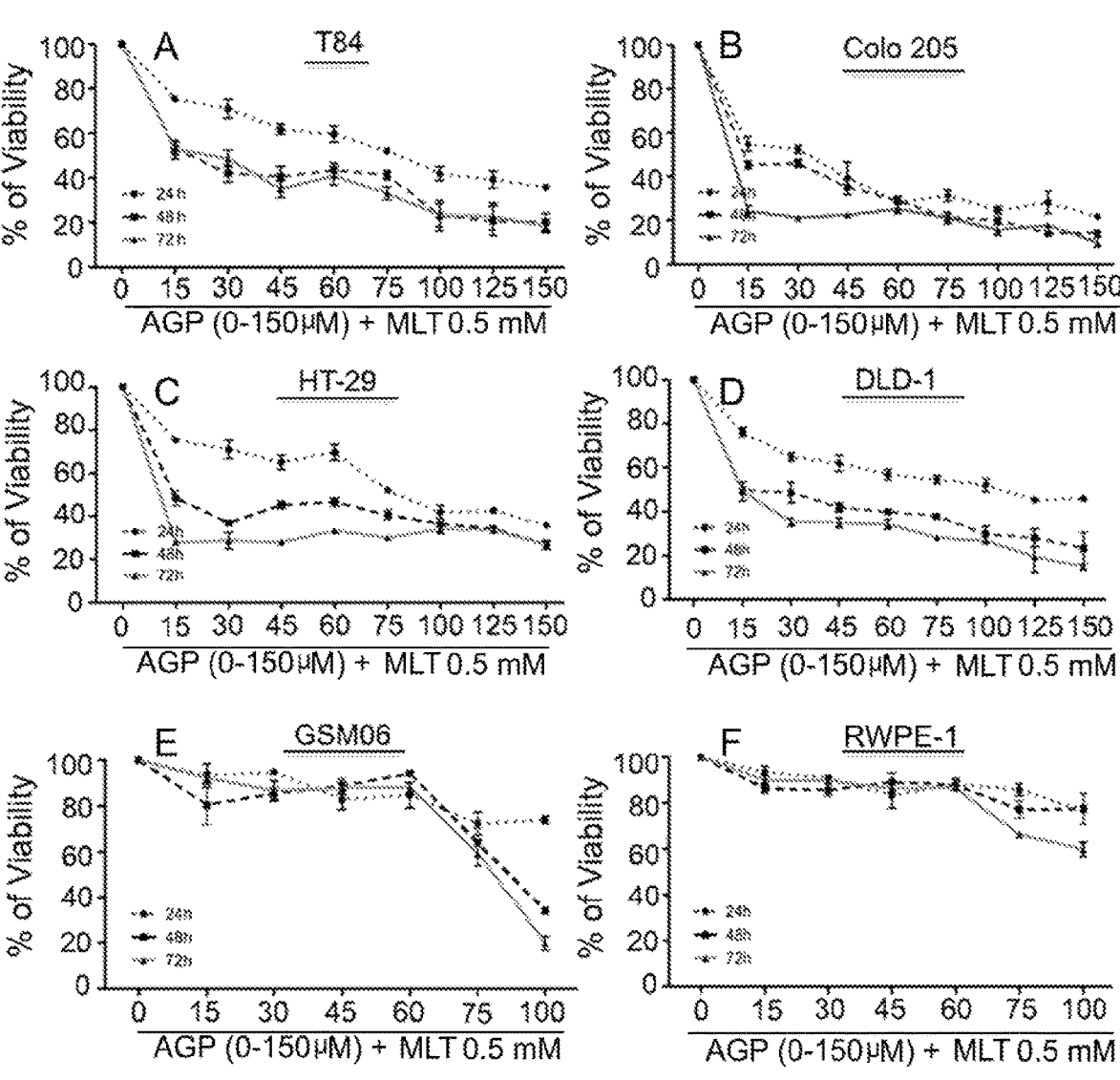

FIG. 8. Impact of AGP and MLT on mCRC cell viability. A. T84, B. Colo 205, C. HT-29, D. DLD-1 E. GSM06

(gastric surface mice mucous), and F. RWPE-1 (prostate epithelial cells were treated with indicated concentration of AGP (0-150 μM), and MLT (0.5 mM) for 24 h, 48 h, and 72 h. Cell viability was quantified using the MTT assay.

Figure 9:
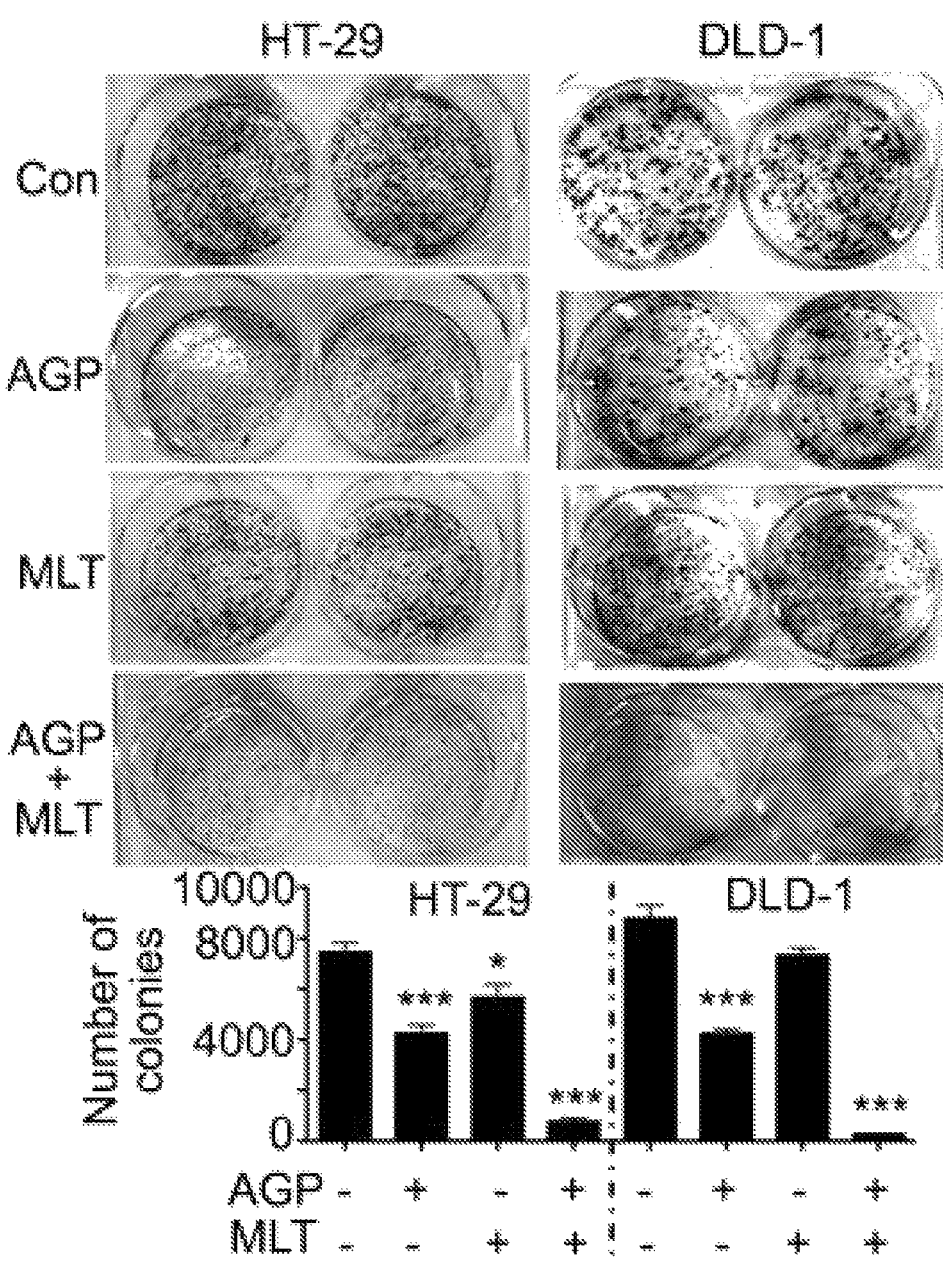

FIG. 9. Co-treatment suppress clonogenicity in HT-29 and DLD-1 cells. HT-29 and DLD-1 cells were diluted and treated with AGP and MLT as indicated dose. Growth was measured by direct counting of clonal clusters stained in multiwell plates with crystal violet at 48 h. Representative micrographs are shown.

Figure 3:
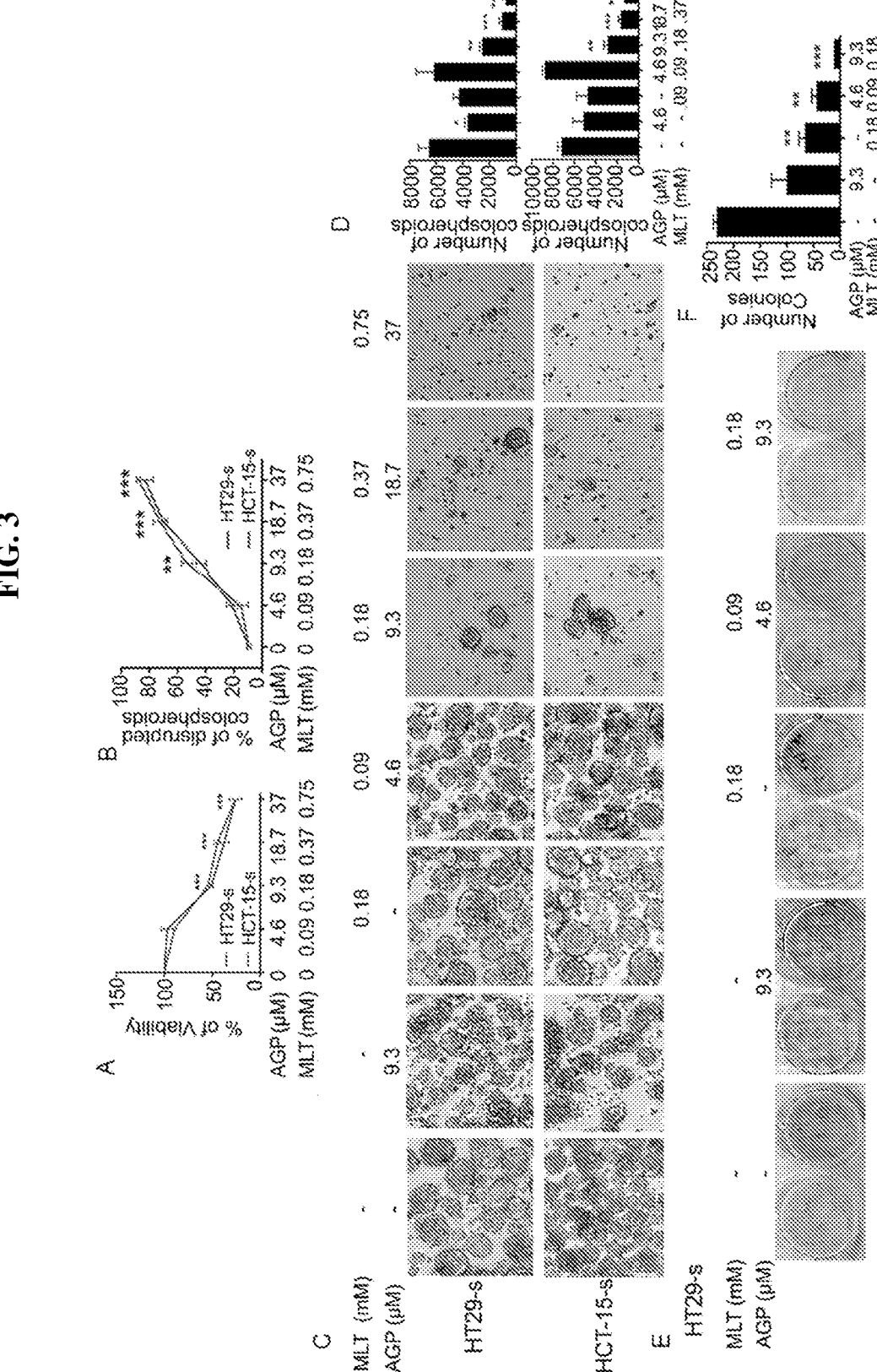
FIG. 3. Synergistically AGP and MLT inhibits colospheroids viability and clonogenicity.
Figure 10:
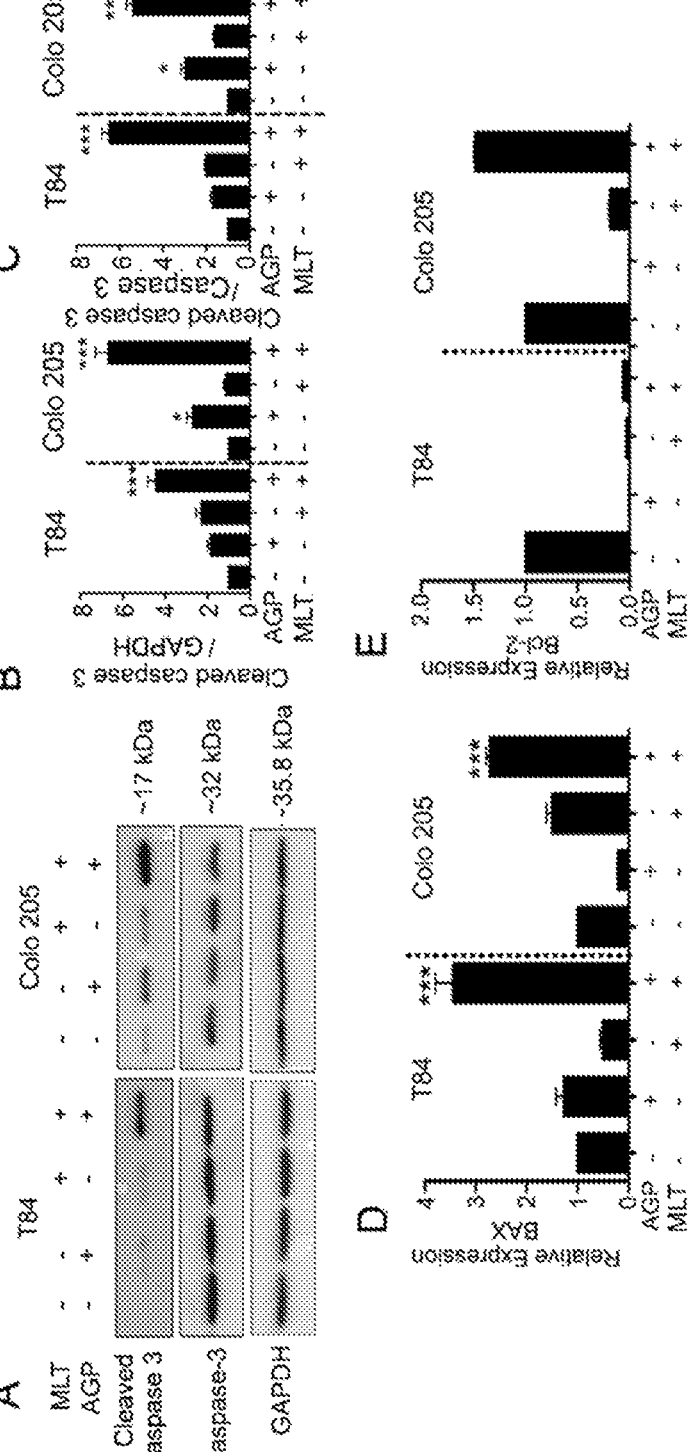

FIG. 10. Co-treatment of AGP and MLT induced cell apoptosis. T84 and Colo 205 cells were treated with or without AGP and MLT at $IC_{50}$ for 48 h and protein expression was determined by immunoblotting for Cleaved caspase 3 (A, upper lane), Caspase 3 (A, middle lane) and GAPDH (A, lower lane). Densitometry analysis was performed and normalized with GAPDH expression to determine significant upregulation of indicated proteins (FIGS. 3B and 3C). The mRNA level for apoptosis associated genes was determined by qRT-PCR for BAX (D), Bcl-2 (E). Bar graphs show quantitative results normalized to GAPDH mRNA levels. Results are from three independent experiments. Statistical significance was determined using one way-ANOVA followed by Bonferroni test (*P<0.05, P<0.01, *P<0.001).

Figure 11:
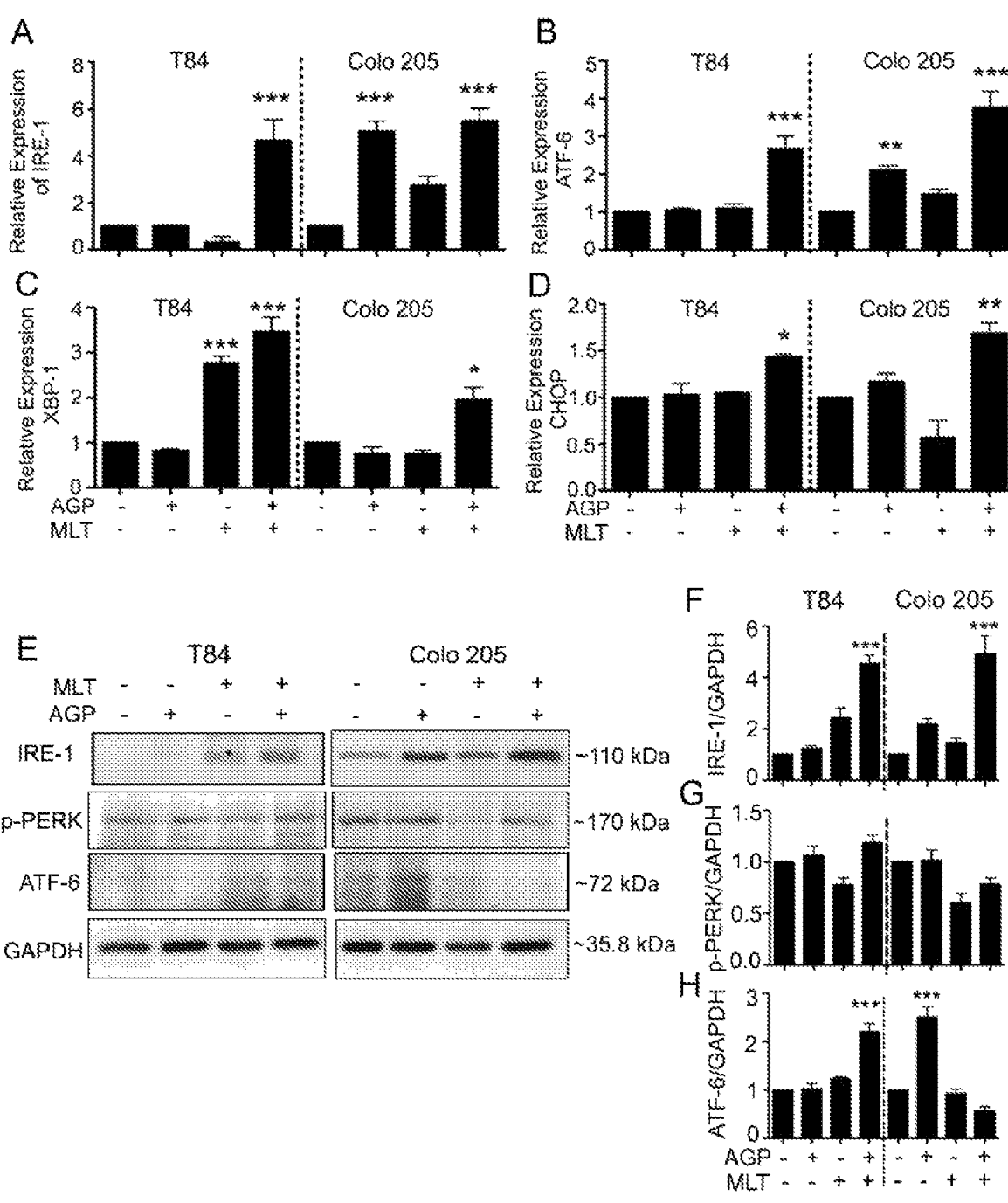

FIG. 11. AGP and MLT induces ER stress-related IRE-1 and associated proteins. T84 and Colo 205 cells were treated as mentioned earlier. The transcriptional level of expression for ER stress associated genes was determined by qRT-PCR for A. IRE-1, B. ATF-6, C. XBP-1 and D. CHOP. Bar graphs show quantitative results normalized to GAPDH mRNA levels. The primary ER transducer translational level was determined by immunoblotting for E. IRE-1 (level 1), p-PERK (level-2), and ATF-6 (level-3). Densitometry analysis was performed and normalized with GAPDH (blot 4). Results are from three independent experiments. Statistical significance was determined using one way-ANOVA followed by Bonferroni test. (*P<0.05, P<0.01, *P<0.001).

Figure 12:
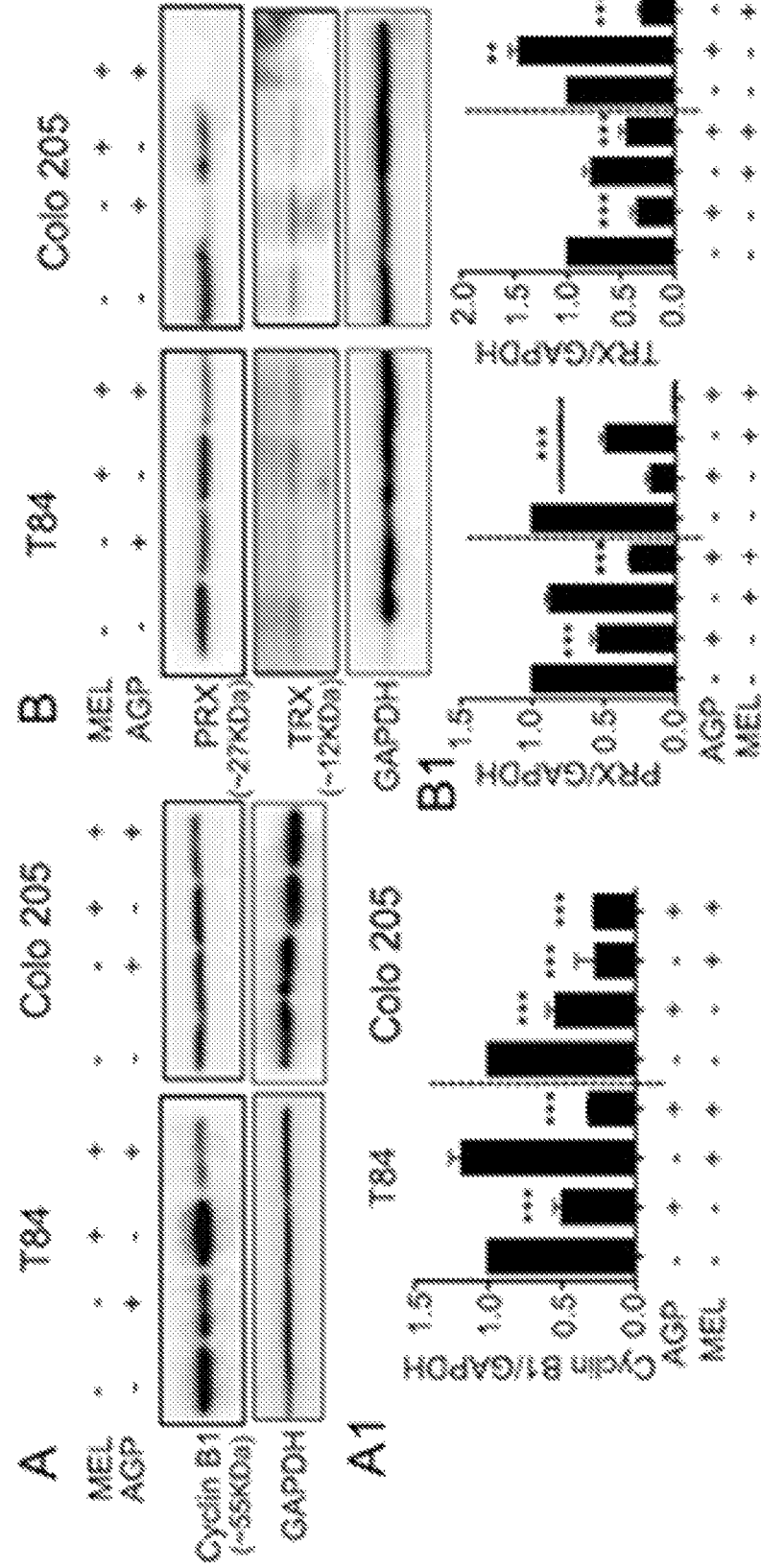

FIG. 12. Co-treatment induced cell cycle arrest and decreased antioxidant protein expression in CRC cells. T84 and Colo 205 cells were treated with or without AGP (15 μM) and MEL (0.5 mM) for 48 h. Cell lysates were analyzed by immunoblot for cyclin B1 (A), PRX (B, upper lane), and TRX (B, middle lane) and quantified by densitometry for expression of A1. Cyclin B1, B1 (left) PRX and (right) TRX. Expression is normalized against GAPDH expression. Statistical significance was determined using one way-ANOVA followed by Bonferroni test (*P<0.05, P<0.01, *P<0.001).

Figure 13:
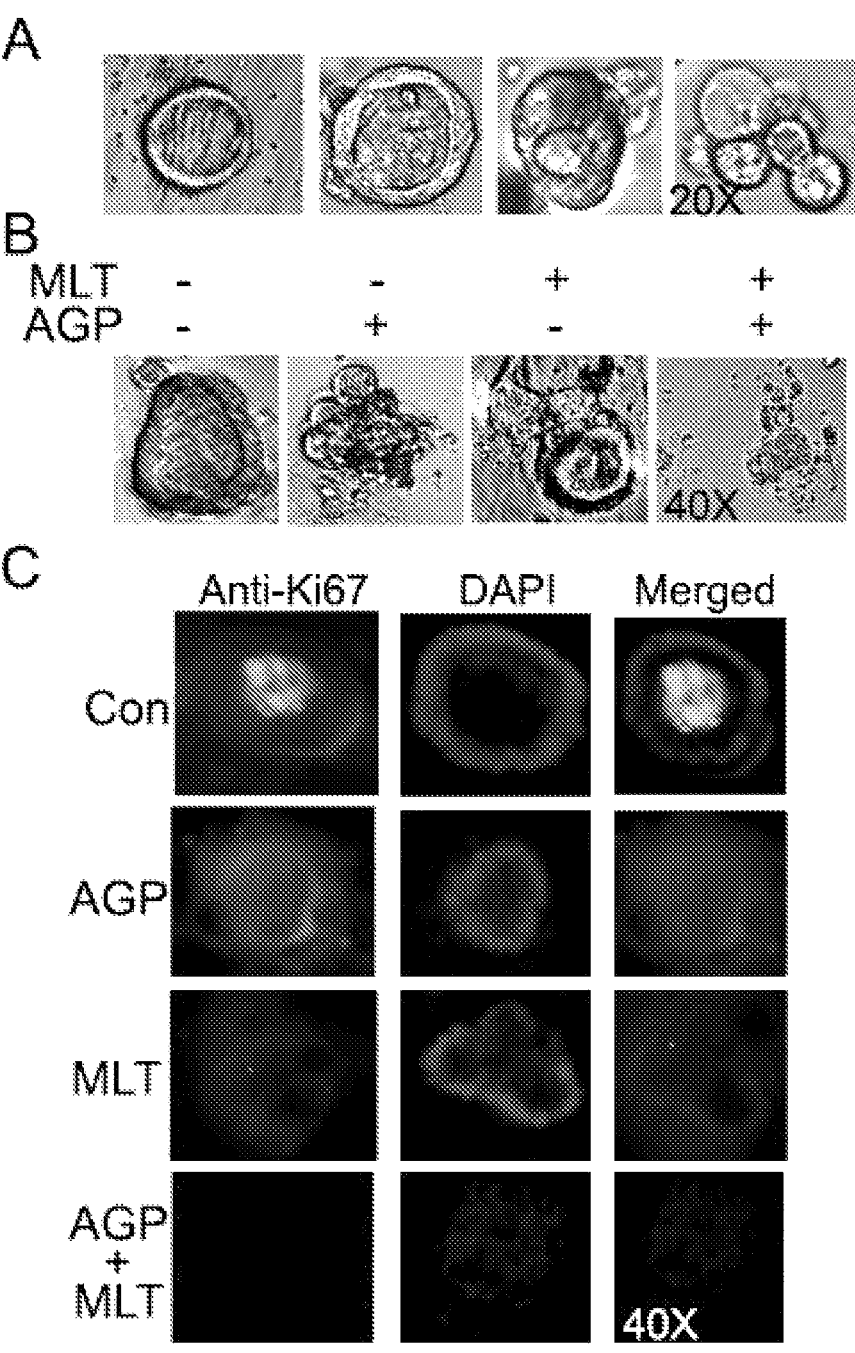

FIG. 13. Impact of AGP and MLT on patient-derived organoids (PDOD). A. Chronological development of PDOD in Matrigel droplet. Organoid structures were confirmed using an inverted light microscope. B. PDOD were treated with or without AGP or MLT and morphology was assessed by light microscopy. C. FITC labeled anti-Ki-67 and DAPI staining of PDOD in the presence or absence of AGP or MLT evaluated by fluorescence microscopy.

DETAILED DESCRIPTION OF THE INVENTION

CRC recurrence is aggressive and therapy resistant. Conventional therapies affect only cancer cells that are proliferating and differentiated from the tumor mass and do not kill the cancer stem cells (CSCs). The CSCs drive tumor recurrence, metastasis, and resistance to chemotherapy, and unencumbered CSCs ultimately result in failed cancer therapy.

Here, the present inventors disclose a combination of AGP (15 μM, 3 times lower than single AGP dose) and melatonin (MLT, 0.5 mM) that treats mCRC, CSCs isolated from colon cancer cells (HT29-s and HCT-15-s) and patient derived organoid models (PDOD) as assessed by cell viability and proliferation measurements. The effect of the dual therapy is almost negligible to the viability of normal cells (viability >96%). Moreover, the dual therapy limits CRC colony formation and CSC formation and disrupts the PDOD membrane integrity along with a decreased Ki-67 expression and fragmented CSCs nuclear morphology. (Expression of the human Ki-67 protein is associated with cell proliferation.) Without being limited by theory, the molecular mechanism seems to be the alteration of inositol-requiring enzyme 1 (IRE-1) in CRC and CSC cells, along with a decreased level of Nanog (a pluripotency transcription factor implicated in proliferation of cancer cells), Oct4, Sox2 (specific colon cancer stem cell markers) and melatonin receptor-2 in CSCs cells. This combinational therapy (AGP+ MLT) can provide new therapeutic modalities that can reduce morbidity and increase the overall survival of CRC patients. This is the first report to demonstrate that AGP and MLT co-treatment promotes cell death of mCRC and CSCs.

Results herein show in this combinatorial approach that the pharmacological concentration can be significantly reduced, by about three-fold, in comparison with standalone AGP (30 μM). Moreover, this drug combination also significantly diminishes the stemness of CRC-CSCs in comparison with AGP alone. Thus, AGP and MLT in combination can be used as a unique treatment.

The treatment of cancer is expensive and time consuming. Additionally, monotherapy with current drugs has various side effects due to the high drug concentrations needed. Based on the above observations, this combinational therapy (AGP+MLT) is expected to reduce the cost of cancer treatment and associated adverse events considerably. In addition, there is a real limitation associated with conventional CRC-CSC treatments in that they are responsible for drug resistance, metastasis and disease recurrence. The five-year survival rate for patients with advanced stage CRC is 14%. The presently reported studies show the impact of co-treatment with AGP and MLT on CSCs-reduced stem cell size and viability and a loss of membrane integrity for PDODs are observed. By overcoming the drug resistance resulting from conventional colon cancer therapy, this combinational therapy will increase the survival rate and quality of life of colon cancer patients. The use of a combination of AGP and MLT in CRC therapy has the potential to act on CSCs in a way that reduces drug resistance, metastasis and disease recurrence.

Reference will now be made in detail to embodiments of the invention which, together with the drawings and the following examples, serve to explain the principles of the invention. These embodiments are described in sufficient detail to enable those skilled in the art to practice the invention, and it is understood that other embodiments may be utilized, and that structural, biological, and chemical changes may be made without departing from the spirit and scope of the present invention. Unless defined otherwise, all technical and scientific terms used herein have the same meanings as commonly understood by one of ordinary skill in the art.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. Furthermore, where the description of one or more embodiments uses the term "comprising," those skilled in the art would understand that, in some specific instances, the embodiment or embodiments can be alternatively described using the language "consisting essentially of" and/or "consisting of." As used herein, the term "about" means at most plus or minus 10% of the numerical value of the number with which it is being used.

It is contemplated that any method or composition described herein can be implemented with respect to any other method or composition described herein.

One skilled in the art may refer to general reference texts for detailed descriptions of known techniques discussed herein or equivalent techniques. These texts include *Current Protocols in Molecular Biology* (Ausubel et. al., eds. John Wiley & Sons, N.Y. and supplements thereto), *Current Protocols in Immunology* (Coligan et al., eds., John Wiley St Sons, N.Y. and supplements thereto), *Current Protocols in Pharmacology* (Enna et al., eds. John Wiley & Sons, N.Y. and supplements thereto) and *Remington: The Science and Practice of Pharmacy* (Lippincott Williams & Wilicins, 2Vt edition (2005)), for example.

As used herein, the terms "effective amount" or "therapeutically effective amount" are interchangeable and refer to an amount that results in an improvement or remediation of at least one symptom of the disease or condition. Those of skill in the art understand that the effective amount may improve the patient's or subject's condition but may not be a complete cure of the disease and/or condition.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject. In some embodiments, the subject has cancer such as colon cancer.

As used herein, the term "inhibit" refers to the ability of the compound to block, partially block, interfere with, decrease, reduce or deactivate a process such as cancer cell proliferation. Thus, one of skill in the art understands that the term "inhibit" encompasses a complete and/or partial loss of, for example, proliferation activity of CRC cells. Cells may be said to be inhibited if their proliferation is fully or partially curtailed or if they are prevented from carrying out the functions that would usually be observed in the absence of the inhibiting condition or material. A chemical substance may be said to be inhibited in the present context if there is full or partial interference with or blockage of its usual function.

The term "preventing" as used herein refers to minimizing, reducing or suppressing the risk of developing a disease state or parameters relating to the disease state or progression or other abnormal or deleterious conditions.

The terms "treating" and "treatment" as used herein refer to administering to a subject a therapeutically effective amount of a composition so that the subject has an improvement in the disease or condition. The improvement is any observable or measurable improvement. Thus, one of skill in the art realizes that a treatment may improve the patient's condition, but may not be a complete cure of the disease. Treating may also comprise treating subjects at risk of developing a disease and/or condition.

As used herein, the symbol "$IC_{50}$" refers to the half maximal inhibitory concentration, a measure of the effectiveness of a substance in inhibiting a biological or biochemical function, such as the viability of CRC cells.

The invention is based on the surprising discovery that colon cancer stem cells can be targeted with dual andrographolide (AGP) and melatonin (MLT) combination therapy.

In some embodiments of the invention, provided are methods and compositions for treating and/or preventing cancer in a subject. In some embodiments, the cancer is colon cancer. In some embodiments, the present invention provides a method of treating cancer in a subject in need thereof, comprising administering to the subject an effective amount of a combination of andrographolide (AGP) and melatonin (MLT).

"Cancer" refers to leukemias, lymphomas, carcinomas, and other malignant tumors of potentially unlimited growth that can expand locally by invasion and potentially systemically by metastasis. Examples of cancers include, but are not limited to, cancer of the adrenal gland, bone, brain, breast, bronchi, colon and/or rectum, gallbladder, head and neck, kidneys, larynx, liver, lung, neural tissue, pancreas, prostate, parathyroid, skin, stomach, and thyroid. Certain other examples of cancers include, acute and chronic lymphocytic and granulocytic tumors, adenocarcinoma, adenoma, basal cell carcinoma, cervical dysplasia and in situ carcinoma, Ewing's sarcoma, epidermoid carcinomas, giant cell tumor, glioblastoma multiforma, hairy-cell tumor, intestinal ganglioneuroma, hyperplastic corneal nerve tumor, islet cell carcinoma, Kaposi's sarcoma, leiomyoma, leukemias, lymphomas, malignant carcinoid, malignant melanomas, malignant hypercalcemia, marfanoid habitus tumor, medullary carcinoma, metastatic skin carcinoma, mucosal neuroma, myeloma, mycosis fungoides, neuroblastoma, osteo sarcoma, osteogenic and other sarcoma, ovarian tumor, pheochromocytoma, polycythermia vera, primary brain tumor, small-cell lung tumor, squamous cell carcinoma of both ulcerating and papillary type, hyperplasia, seminoma, soft tissue sarcoma, retinoblastoma, rhabdomyosarcoma, renal cell tumor, topical skin lesion, veticulum cell sarcoma, and Wilm's tumor. In some embodiments, the cancer is melanoma, breast cancer, prostate cancer or colon cancer.

In some embodiments, the cancer to be treated is colon cancer or colorectal cancer (CRC).

In some embodiments, the combination of andrographolide and melatonin is synergistic. A synergistic effect is a biological response to exposure to multiple chemicals (agents) which is greater than the sum of the effects of the individual agents. It is an effect that occurs when two or more agents (for example medications) have a more powerful effect when used together than either has been used alone.

Figure 1:
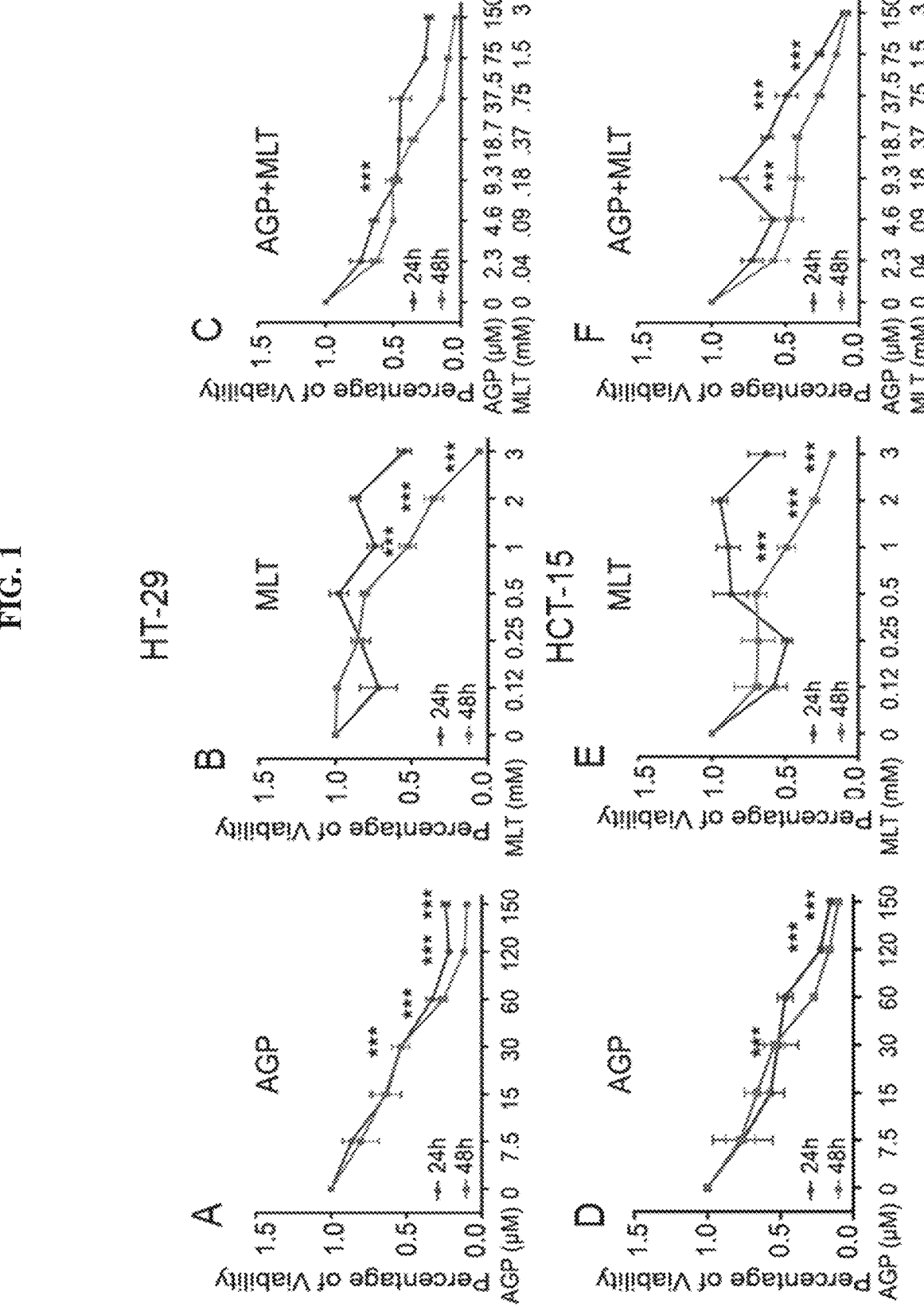
FIG. 1: Impact of single and combined doses of AGP and MLT on m-CRC cell viability. HT-29 (A-C) and HCT-15 (D-F) cells were treated with the indicated concentration of AGP (0-150 μM, A, D), MLT (0-3 mM, B, E), or both (C and F) for 24 h and 48 h. Cell viability was quantified using the MTT assay. Experiments were performed three times ($***P<0.001$).
Figure 2:
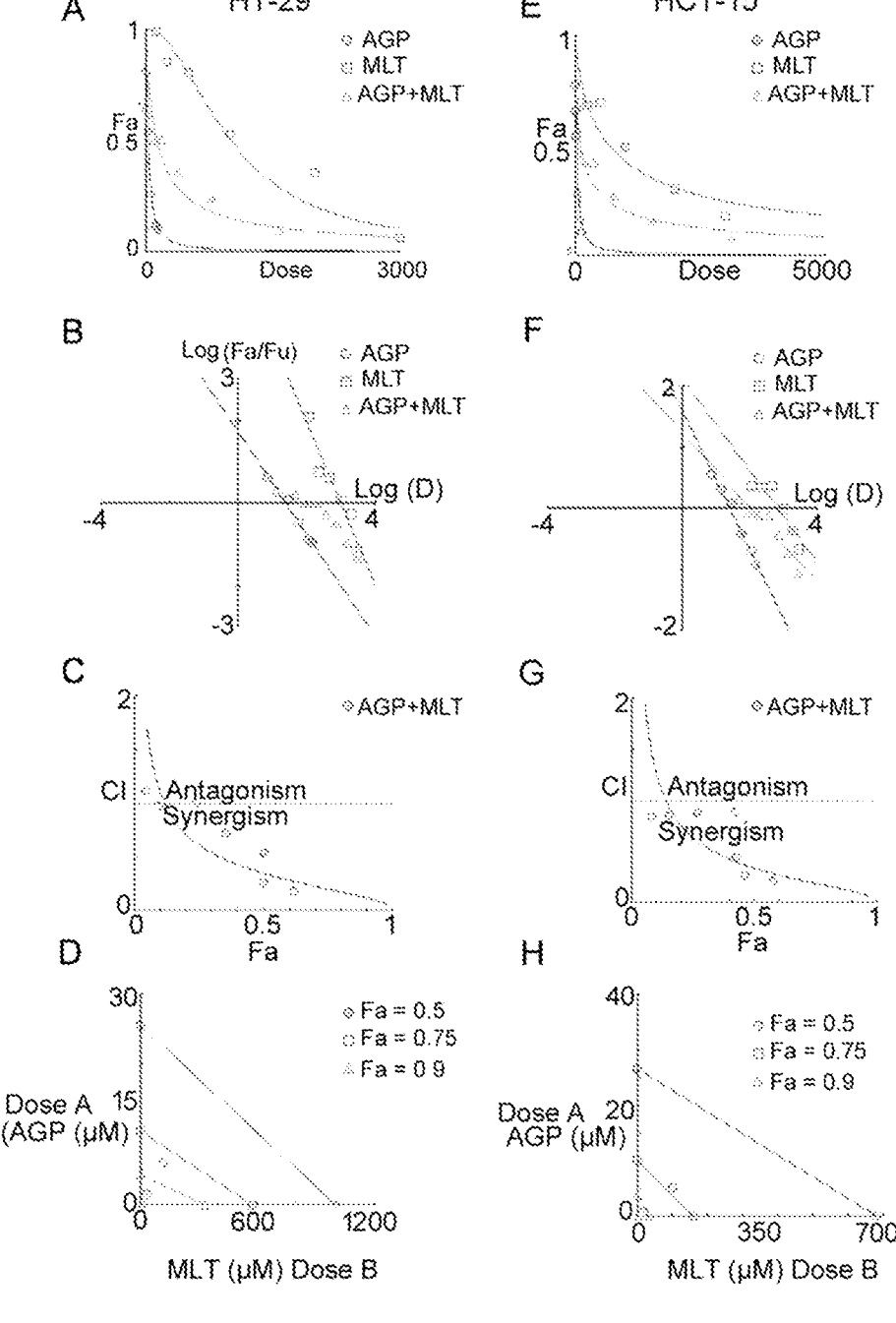
FIG. 2. The graphic representations obtained from the CompuSyn Report for AGP and MLT and its combinations at 48 h. Dose-effect curve demonstrates the relationship between Fa and Dose; (A, E, HT-29, HCT-15). Median-effect (ME) plot B (HT-29) and F (HCT-15) demonstrates a remapping of the dose-effect curve in order to derive the $IC_{50}$ value. The value can be obtained from the X-intercept of the ME plot. The ME dose at the $IC_{50}$ value indicates "potency". The Combination index plot C (HT-29) represents 7 combination data points, 5 of which demonstrate a synergistic relationship (CI<1) and the other 2 of which describe an additive relationship. Plot G (HCT-15) represents 7 combination data points, all of which demonstrate a synergistic relationship (CI<1). The simulation at low Fa showed substantial antagonism. Isobologram for 50%, 75% and 90% inhibitions are shown (D, H, HT-29 and HCT-15). AGP+MLT data points on the diagonal line indicate additive effects, on the lower left indicate synergism, on the upper right indicate antagonism. In this case, $IC_{50}$, $IC_{75}$, and $IC_{90}$ indicate synergism.

Numerous experiments reported herein support the proposition that the latter combination will be an effective treatment for cancer, such as CRC. As shown in FIGS. 1 and 2 and explained in the Examples below, co-treatment in vitro of CRC cells with a combination of AGP and MLT inhibits cell viability much better than does either AGP or MLT alone. That the co-treatment has little or no effect on normal human cells is also apparent from the data. Moreover, much lower doses of AGP and MLT are needed for effective killing of CRC cells than are required when either AGP or MLT is used alone.

As shown herein, co-treatment with a combination of AGP and MLT is associated with increased levels of chemical markers that indicate endoplasmic reticulum (ER) stress in the CRC cells. The data is consistent with a co-treatment that will be effective against CRC, and more so than is either AGP or MLT alone.

Co-treatment down regulates Cyclin B1, which is associated with mitosis and thus CRC cell proliferation. Antioxidant proteins are upregulated, and this is again consistent with a co-treatment that limits CRC cell proliferation.

Stem cells are known to be important in metastasis, and co-treatment physically breaks up the spheroid structure of CRC stem cells. This supports that the co-treatment will inhibit metastasis. Chemical markers associated with CRC CSCs are present at much lower levels after co-treatment.

It is further shown herein that by monitoring the effects on the concentrations of various chemical markers, the co-treatment favors cell death (apoptosis), inhibits angiogenesis (blood vessel formation associated with cell proliferation) and diminishes the "stemness" of CSCs (associated with metastasis). The co-treatment was shown to overcome resistance to the anticancer drug 5-fluorouracil among CRC cells. Co-treatment is also disruptive to patient derived organoids.

The combination of therapeutic agents that inhibits the proliferation of cancer cells and cancer stem cells can be administered in a variety of ways, and the mode of administration is not particularly limiting. In some embodiments, at least one of the agents (or the combination) is administered directly (topically), intravenously, subcutaneously, transcutaneously, intrathecally, intramuscularly, intracutaneously, intragastrically or orally.

In some embodiments, the invention provides a composition for treating cancer in a subject, comprising an effective amount of a combination of AGP and MLT and a pharmaceutically acceptable carrier. In some embodiments the combination of agents inhibits proliferation of CSCs.

In some embodiments, an effective amount of AGP in the combination of AGP and MLT that is administered includes a dose of about 1.0 μM to about 150 μM. In some embodiments, an amount of AGP administered is from about 5.0 μM to about 50 μM; about 7.5 μM to about 25 μM; about 10 μM to about 20 μM; about 10 μM to about 15 μM; about 25 μM to about 30 μM; about 30 μM to about 35 μM; about 35 μM to about 40 μM; about 40 μM to about 45 μM; about 45 μM to about 50 μM; about 50 μM to about 55 μM; about 55 μM to about 60 μM; about 60 μM to about 70 μM; about 70 μM to about 80 μM; about 80 μM to about 90 μM; about 90 μM to about 110 μM; about 110 μM to about 130 μM; and about 130 μM to about 150 μM. Of course, all of these amounts are exemplary, and any amount in-between these points is also expected to be of use in the invention.

In some embodiments, an effective amount of MLT in the combination of AGP and MLT that is administered includes a dose of about 10 µM to about 3000 µM. In some embodiments, an amount of MLT administered is from about 25 µM to about 250 µM; about 250 µM to about 350 µM; about 350 µM to about 450 µM; about 450 µM to about 550 µM; about 550 µM to about 650 µM; about 650 µM to about 750 µM; about 750 µM to about 850 µM; about 850 µM to about 950 µM; about 950 µM to about 1100 µM; about 1100 µM to about 1300 µM; about 1300 µM to about 1500 µM; about 1500 µM to about 1700 µM; about 1700 µM to about 1900 µM; about 1900 µM to about 2100 µM; about 2100 µM to about 2300 µM; about 2300 µM to about 2600 µM; and about 2600 µM to about 3000 µM. Of course, all of these amounts are exemplary, and any amount in-between these points is also expected to be of use in the invention.

In some embodiments, an effective amount of AGP in the combination of AGP and MLT that is administered includes a dose of about 0.005 g to about 5 g. In some embodiments, an amount of AGP administered is from about 0.05 g to about 5 g. In some embodiments, an amount of AGP administered is from about 0.05 g to about 0.3 g; about 0.3 g to about 0.5 g; about 0.5 g to about 0.7 g; about 0.7 g to about 0.9 g; about 0.9 g to about 1.2 g; about 1.2 g to about 1.5 g; about 1.5 g to about 1.8 g; about 1.8 g to about 2.1 g; about 2.1 g to about 2.4 g; about 2.4 g to about 2.7 g; about 2.7 g to about 3.0 g; about 3.0 g to about 3.3 g; about 3.3 g to about 3.6 g; about 3.6 g to about 3.9 g; about 3.9 g to about 4.2 g; about 4.2 g to about 4.5 g; and about 4.5 g to about 5.0 g. Of course, all of these amounts are exemplary, and any amount in-between these points is also expected to be of use in the invention.

In some embodiments, an effective amount of MLT in the combination of AGP and MLT that is administered includes a dose of about 0.0005 g to about 10 g. In some embodiments, an effective amount of MLT in the combination of AGP and MLT that is administered includes a dose of about 0.001 g to about g. In some embodiments, an amount of MLT administered is from about 0.25 g to about 0.7 g; about 0.7 g to about 1.0 g; about 1.0 g to about 1.5 g; about 1.5 g to about 2.0 g; about 2.0 g to about 2.5 g; about 2.5 g to about 3.0 g; about 3.0 g to about 3.5 g; about 3.5 g to about 4.0 g; about 4.0 g to about 4.5 g; about 4.5 g to about 5.0 g; about 5.0 g to about 5.5 g; about 5.5 g to about 6.0 g; about 6.0 g to about 6.5 g; about 6.5 g to about 7.0 g; about 7.0 g to about 8.0 g; about 8.0 g to about 9.0 g; and about 9.0 g to about 10.0 g. Of course, all of these amounts are exemplary, and any amount in-between these points is also expected to be of use in the invention.

In some embodiments, an effective amount of AGP in the combination of AGP and MLT that is administered includes a dose of about 0.1 mg/kg body weight of the subject to about 20 mg/kg body weight of the subject. In some embodiments, an effective amount of AGP in the combination of AGP and MLT that is administered includes a dose of about 1 mg/kg body weight of the subject to about 20 mg/kg body weight of the subject. In some embodiments, an amount of AGP administered is from about 1 mg/kg to about 3 mg/kg; about 3 mg/kg to about 5 mg/kg; about 5 mg/kg to about 7 mg/kg; about 7 mg/kg to about 9 mg/kg; about 9 mg/kg to about 10 mg/kg; about 10 mg/kg to about 11 mg/kg; about 11 mg/kg to about 12 mg/kg; about 12 mg/kg to about 14 mg/kg; about 14 mg/kg to about 16 mg/kg; about 16 mg/kg to about 18 mg/kg; and about 18 mg/kg to about 20 mg/kg. Of course, all of these amounts are exemplary, and any amount in-between these points is also expected to be of use in the invention.

In some embodiments, an effective amount of MLT in the combination of AGP and MLT that is administered includes a dose of about 0.01 mg/kg body weight of the subject to about 250 mg/kg body weight of the subject. In some embodiments, an effective amount of MLT in the combination of AGP and MLT that is administered includes a dose of about 0.1 mg/kg body weight of the subject to about 1 mg/kg body weight of the subject. In some embodiments, an effective amount of MLT in the combination of AGP and MLT that is administered includes a dose of about 10 mg/kg body weight of the subject to about 250 mg/kg body weight of the subject. In some embodiments, an amount of AGP administered is from about 10 mg/kg to about 20 mg/kg; about 20 mg/kg to about 30 mg/kg; about 30 mg/kg to about 40 mg/kg; about 40 mg/kg to about 50 mg/kg; about 50 mg/kg to about 60 mg/kg; about 60 mg/kg to about 80 mg/kg; about 80 mg/kg to about 100 mg/kg; about 100 mg/kg to about 130 mg/kg; about 130 mg/kg to about 160 mg/kg; about 160 mg/kg to about 200 mg/kg; and about 200 mg/kg to about 250 mg/kg. Of course, all of these amounts are exemplary, and any amount in-between these points is also expected to be of use in the invention.

In some embodiments, a weight ratio of AGP to MLT in an effective combination of AGP and MLT can be from about 1:1 to about 1:20. In some embodiments, a weight ratio of AGP to MLT can be from about 1:1 to about 1:2; about 1:2 to about 1:3; about 1:3 to about 1:5; about 1:5 to about 1:7; about 1:7 to about 1:9; about 1:9 to about 1:11; about 1:11 to 1:12; about 1:12 to about 1:13; about 1:13 to about 1:14; about 1:14 to about 1:15; about 1:15 to about 1:17; and about 1:17 to about 1:20. Of course, all of these amounts are exemplary, and any amount in-between these points is also expected to be of use in the invention.

One of skill in the art will understand that exact dosages can depend on the subject patient's health history and/or previous responses to the subject compound(s) or composition(s) and will be ascertainable by a person skilled in the art using known methods and techniques for determining effective doses.

As provided herein, the subject can be administered a single dose or multiple doses of a combination of AGP and MLT. The dose of AGP and MLT can be administered in a single composition or in multiple compositions. Thus, the combined administration includes co-administration, using separate formulations or a single pharmaceutical formulation, and consecutive administration in either order, wherein preferably there is a time period while both active agents simultaneously exert their biological activities. In some embodiments, the dose of AGP and MLT is administered in a single composition. In some embodiments, the single composition comprises an orally administered slow or delayed release tablet or capsule.

In some embodiments, the drug combination can be administered parenterally or alimentarily. Parenteral administrations include, but are not limited to, intravenously, intradermally, transdermally, intramuscularly, intraarterially, intrathecally, subcutaneously, or intraperitoneally. See, e.g., U.S. Pat. Nos. 6,613,308, 5,466,468, 5,543,158; 5,641,515; and 5,399,363 (each specifically incorporated herein by reference in its entirety). Alimentary administrations include, but are not limited to orally, buccally, rectally, or sublingually.

In some embodiments, the administration of the therapeutic compounds of the present invention may include systemic, local and/or regional administrations, for example, topically (dermally, transdermally), via catheters, implantable pumps, dermal patches, transdermal patches, etc. Alternatively, other routes of administration are also contemplated such as, for example, arterial perfusion, intracavitary, intraperitoneal, intrapleural, intraventricular and/or intrathecal. The skilled artisan is capable of determining the appropriate administration route using standard methods and procedures. Other routes of administration are discussed elsewhere in the specification and are incorporated herein by reference.

Treatment methods involve treating an individual with an effective amount of a composition comprising a combination of AGP and MLT. An effective amount is described, generally, as that amount sufficient to detectably and repeatedly ameliorate, reduce, minimize, or limit the extent of a disease or its symptoms. The effective amount of a combination of AGP and MLT to be used includes those amounts effective to produce beneficial results, particularly with respect to amelioration of colon cancer in the recipient animal or patient.

As is well known in the art, a specific dose level of active compounds such as a combination of AGP and MLT for any particular patient depends upon a variety of factors including the activity of the specific compound employed, the age, body weight, general health, sex, diet, time of administration, route of administration, rate of excretion, drug combination, and the severity of the particular disease undergoing therapy.

In some embodiments, the compound(s) or composition (s) can be administered to the subject once, such as by a single injection or deposition at or near the site of interest. In some embodiments, the compound(s) or composition(s) can be administered to a subject over a period of days, weeks, months or even years. In some embodiments, the compound(s) or composition(s) is administered at least once a day to a subject. Where a dosage regimen comprises multiple administrations, it is understood that the effective amount of the compound(s) or composition(s) administered to the subject can comprise the total amount of the compound(s) or composition(s) administered over the entire dosage regimen.

Transcription factors are regulatory proteins that bind to a specific DNA sequence (e.g., promoters and enhancers) and regulate transcription of an encoding DNA region. Thus, transcription factors can be used to modulate the expression of certain materials that are implicated in the proliferation of CSCs. Typically, a transcription factor comprises a binding domain that binds to DNA (a DNA-binding domain) and a regulatory domain that controls transcription. Where a regulatory domain activates transcription, that regulatory domain is designated an activation domain. Where that regulatory domain inhibits transcription, that regulatory domain is designated a repression domain. More specifically, a combination of AGP and MLT can affect levels of transcription factors such as Nanog that are important in the proliferation of CSCs.

In some embodiments, the methods further comprise administration of the combination of AGP and MLT in conjunction with one or more additional treatments or therapies. In some embodiments, the additional therapy is selected from radiation, chemotherapy, surgery, immunotherapy or administration of an anti-cancer therapeutic.

In some embodiments, the additional treatment or therapy includes, for example, administration of an anti-cancer therapeutic, such as, for example, chemotherapy, immunotherapy or an immune checkpoint inhibitor.

In certain embodiments, the additional therapy comprises administration of an agent that is an inhibitor of an immune checkpoint molecule. In one embodiment, the agent is an inhibitor of PD-1, PD-L1, PD-L2, CTLA4, TIM3, LAG3, VISTA, BTLA, TIGIT, LAIR1, CD160, 2B4 and/or TGFR beta. In one embodiment, the inhibitor of an immune checkpoint molecule inhibits PD-1, PD-L1, LAG-3, TIM-3 or CTLA4, or any combination thereof. The term "inhibition" or "inhibitor" includes a reduction in a certain parameter, e.g., an activity, of a given molecule, e.g., an immune checkpoint inhibitor. For example, inhibition of an activity, e.g., a PD-1 or PD-L1 activity, of at least 5%, 10%, 20%, 30%, 40%, 50% or more is included by this term. Thus, inhibition need not be 100%.

In some embodiments, an anti-cancer agent is administered in combination with AGP and MLT. In some embodiments, the anti-cancer agent is selected from the group consisting of Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Adrucil (Fluorouracil), Afatinib Dimaleate, Afinitor (Everolimus), Aldara (Imiquimod), Aldesleukin, Alemtuzumab, Alimta (Pemetrexed Disodium), Aloxi (Palonosetron Hydrochloride), Ambochlorin (Chlorambucil), Ambochlorin (Chlorambucil), Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase *Erwinia chrysanthemi*, Avastin (Bevacizumab), Axitinib, Azacitidine, BEACOPP, Becenum (Carmustine), Beleodaq (Belinostat), Belinostat, Bendamustine Hydrochloride, BEP, Bevacizumab, Bexarotene, Bexxar (Tositumomab and I 131 Iodine Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Busulfan, Busulfex (Busulfan), Cabazitaxel, Cabozantinib-S-Malate, CAF, Campath (Alemtuzumab), Camptosar (Irinotecan Hydrochloride), Capecitabine, CAPDX, Carboplatin, CARBOPLATIN-TAXOL, Carfilzomib, Carmubris (Carmustine), Carmustine, Carmustine Implant, Casodex (Bicalutamide), CeeNU (Lomustine) Ceritinib, Cerubidine (Daunorubicin Hydrochloride), Cervarix (Recombinant HPV Bivalent Vaccine), Cetuximab, Chlorambucil, CHLORAMBUCIL-PREDNISONE, CHOP, Cisplatin, Clafen (Cyclophosphamide), Clofarabine, Clofarex (Clofarabine), Clolar (Clofarabine), CMF, Cometriq (Cabozantinib-S-Malate), COPP, COPP-ABV, Cosmegen (Dactinomycin), Crizotinib, CVP, Cyclophosphamide, Cyfos (Ifosfamide), Cyramza (Ramucirumab), Cytarabine, Cytarabine, Liposomal, Cytosar-U (Cytarabine), Cytoxan (Cyclophosphamide), Dabrafenib, Dacarbazine, Dacogen (Decitabine), Dactinomycin, Dasatinib, Daunorubicin Hydrochloride, Decitabine, Degarelix, Denileukin Diftitox, Denosumab, DepoCyt (Liposomal Cytarabine), DepoFoam (Liposomal Cytarabine), Dexrazoxane Hydrochloride, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Efudex (Fluorouracil), Elitek (Rasburicase), Ellence (Epirubicin Hydrochloride), Eloxatin (Oxaliplatin), Eltrombopag Olamine, Emend (Aprepitant), Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase *Erwinia chrysanthemi*), Etopophos (Etoposide Phosphate), Etoposide, Etoposide Phosphate, Evacet (Doxorubicin Hydrochloride Liposome), Everolimus, Evista (Raloxifene Hydrochloride), Exemestane, Fareston

15

(Toremifene), Faslodex (Fulvestrant), FEC, Femara (Letrozole), Filgrastim, Fludara (Fludarabine Phosphate), Fludarabine Phosphate, Fluoroplex (Fluorouracil), Fluorouracil, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Ifex (Ifosfamide), Ifosfamide, Ifosfamidum (Ifosfamide), Imatinib Mesylate, Imbruvica (Ibrutinib), Imiquimod, Inlyta (Axitinib), Intron A (Recombinant Interferon Alfa-2b), Iodine 131 Tositumomab and Tositumomab, Ipilimumab, Iressa (Gefitinib), Irinotecan Hydrochloride, Istodax (Romidepsin), Ixabepilone, Ixempra (Ixabepilone), Jakafi (Ruxolitinib Phosphate), Jevtana (Cabazitaxel), Kadcyla (Ado-Trastuzumab Emtansine), Keoxifene (Raloxifene Hydrochloride), Kepivance (Palifermin), Keytruda (Pembrolizumab), Kyprolis (Carfilzomib), Lanreotide Acetate, Lapatinib Ditosylate, Lenalidomide, Lenvatinib Mesylate, Lenvima (Lenvatinib Mesylate), Letrozole, Leucovorin Calcium, Leukeran (Chlorambucil), Leuprolide Acetate, Levulan (Aminolevulinic Acid), Linfolizin (Chlorambucil), LipoDox (Doxorubicin Hydrochloride Liposome), Liposomal Cytarabine, Lomustine, Lupron (Leuprolide Acetate), Lupron Depot (Leuprolide Acetate), Lupron Depot-Ped (Leuprolide Acetate), Lupron Depot-3 Month (Leuprolide Acetate), Lupron Depot-4 Month (Leuprolide Acetate), Lynparza (Olaparib), Marqibo (Vincristine Sulfate Liposome), Matulane (Procarbazine Hydrochloride), Mechlorethamine Hydrochloride, Megace (Megestrol Acetate), Megestrol Acetate, Mekinist (Trametinib), Mercaptopurine, Mesna, Mesnex (Mesna), Methazolastone (Temozolomide), Methotrexate, Methotrexate LPF (Methotrexate), Mexate (Methotrexate), Mexate-AQ (Methotrexate), Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Nelarabine, Neosar (Cyclophosphamide), Neupogen (Filgrastim), Nexavar (Sorafenib Tosylate), Nilotinib, Nivolumab, Nolvadex (Tamoxifen Citrate), Nplate (Romiplostim), Obinutuzumab, OEPA, Ofatumumab, OFF, Olaparib, Omacetaxine Mepesuccinate, Oncaspar (Pegaspargase), Ontak (Denileukin Diftitox), Opdivo (Nivolumab), OPPA, Oxaliplatin, Paclitaxel, Paclitaxel Albumin-stabilized Nanoparticle Formulation, PAD, Palbociclib, Palifermin, Palonosetron Hydrochloride, Pamidronate Disodium, Panitumumab, Paraplat (Carboplatin), Paraplatin (Carboplatin), Pazopanib Hydrochloride, Pegaspargase, Peginterferon Alfa-2b, PEG-Intron (Peginterferon Alfa-2b), Pembrolizumab, Pemetrexed Disodium, Perj

16 eta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Pralatrexate, Prednisone, Procarbazine Hydrochloride, Proleukin (Aldesleukin), Prolia (Denosumab), Promacta (Eltrombopag Olamine), Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, R-EPOCH, Revlimid (Lenalidomide), Rheumatrex (Methotrexate), Rituxan (Rituximab), Rituximab, Romidepsin, Romiplostim, Rubidomycin (Daunorubicin Hydrochloride), Ruxolitinib Phosphate, Sclerosol Intrapleural Aerosol (Talc), Siltuximab, Sipuleucel-T, Somatuline Depot (Lanreotide Acetate), Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synovir (Thalidomide), Synribo (Omacetaxine Mepesuccinate), TAC, Tafinlar (Dabrafenib), Talc, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Temodar (Temozolomide), Temozolomide, Temsirolimus, Thalidomide, Thalomid (Thalidomide), Thiotepa, Toposar (Etoposide), Topotecan Hydrochloride, Toremifene, Torisel (Temsirolimus), Tositumomab and I 131 Iodine Tositumomab, Totect (Dexrazoxane Hydrochloride), TPF, Trametinib, Trastuzumab, Treanda (Bendamustine Hydrochloride), Trisenox (Arsenic Trioxide), Tykerb (Lapatinib Ditosylate), Vandetanib, VAMP, Vectibix (Panitumumab), VeIP, Velban (Vinblastine Sulfate), Velcade (Bortezomib), Velsar (Vinblastine Sulfate), Vemurafenib, VePesid (Etoposide), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Voraxaze (Glucarpidase), Vorinostat, Votrient (Pazopanib Hydrochloride), Wellcovorin (Leucovorin Calcium), Xalkori (Crizotinib), Xeloda (Capecitabine), XELIRI, Xgeva (Denosumab), Xofigo (Radium 223 Dichloride), Xtandi (Enzalutamide), Yervoy (Ipilimumab), Zaltrap (Ziv-Aflibercept), Zelboraf (Vemurafenib), Zevalin (Ibritumomab Tiuxetan), Zinecard (Dexrazoxane Hydrochloride), Ziv-Aflibercept, Zoladex (Goserelin Acetate), Zoledronic Acid, Zolinza (Vorinostat), Zometa (Zoledronic Acid), Zydelig (Idelalisib), Zykadia (Ceritinib), and Zytiga (Abiraterone Acetate).

When employed in combination, the additional therapy/treatment may be administered prior to, during, and/or subsequent to the administration of the combination of AGP and MLT.

In one embodiment, the additional therapy comprises administration of an agent that inhibits Nanog. An antisense molecule that binds to a translational or transcriptional start site, or splice junctions, is an ideal inhibitor. Antisense, ribozyme, and double-stranded RNA molecules target a particular sequence to achieve a reduction or elimination of a particular polypeptide, such as Nanog. Thus, it is contemplated that antisense, ribozyme, and double-stranded RNA, and RNA interference molecules are constructed and used to modulate Nanog expression.

The present invention also contemplates therapeutic methods employing compositions comprising the active substances disclosed herein. Preferably, these compositions include pharmaceutical compositions comprising a therapeutically effective amount of one or more of the active compounds or substances along with a pharmaceutically acceptable carrier.

As used herein, the term "pharmaceutically acceptable" carrier means a non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations.

Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Examples of pharmaceutically acceptable antioxidants include, but are not limited to, water soluble antioxidants such as ascorbic acid, cysteine hydrochloride, sodium bisulfite, sodium metabisulfite, sodium sulfite, and the like; oil soluble antioxidants, such as ascorbyl palmitate, butylated hydroxyanisole (BHA), butylated hydroxytoluene (BHT), lecithin, propyl gallate, alphatocopherol and the like; and the metal chelating agents such as citric acid, ethylenediamine tetraacetic acid (EDTA), sorbitol, tartaric acid, phosphoric acid and the like.

In some embodiments, the total thrice weekly dose of the active compounds of the present invention administered to a subject in single or in divided doses can be in amounts, for example, from 1 to 20 mg/kg body weight of AGP and from 10 to 250 mg/kg body weight of MLT, or more usually from 2 to 4 mg/kg body weight of AGP and from 25 to 50 mg/kg body weight of MLT. Single dose compositions may contain such amounts or submultiples thereof to make up the dose allocated for thrice weekly administration. In general, treatment regimens according to the present invention comprise administration to a human or other mammal in need of such treatment from about 50 mg to about 3500 mg of AGP and from about 500 mg to about 15,000 mg of MLT three times weekly in multiple doses or in a single dose of about 50 mg, 80 mg, 150 mg, 300 mg, 600 mg, 1000 mg, 2000 mg, or 3500 mg of AGP with about 500 mg, 750 mg, 1000 mg, 2000 mg, 3000 mg, 5000 mg, 8000 mg, or 15,000 mg of MLT.

For example, in one embodiment of the present invention directed to a method of treating cancer, such as targeting colon cancer stem cells, with dual andrographolide and melatonin combination therapy in a subject by administering to the subject a formulation containing an effective amount of a combination of AGP and MLT and a pharmaceutically acceptable carrier. In some embodiments, such formulations may contain from about 0.1 to about 5 grams of AGP and from about 0.5 to about 10 grams of MLT. In some embodiments, such formulations may contain from about 0.001 to about 5 grams of AGP and from about 0.001 to about 10 grams of MLT.

The active agents of the present invention can be administered alone or in combination with one or more active pharmaceutical agents. In some embodiments, the one or more active pharmaceutical agents are useful to treat cancer, such as colon cancer with dual andrographolide and melatonin combination therapy in the subject.

Liquid dosage forms for oral administration may include pharmaceutically acceptable emulsions, microemulsions, solutions, suspensions, syrups and elixirs containing inert diluents commonly used in the art, such as water, isotonic solutions, or saline. Such compositions may also comprise adjuvants, such as wetting agents; emulsifying and suspending agents; sweetening, flavoring and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable formulation can be sterilized, for example, by filtration through a bacteria-retaining filter, or by incorporating sterilizing agents in the form of sterile solid compositions, which can be dissolved or dispersed in sterile water or other sterile injectable medium just prior to use.

In order to prolong the effect of a drug, it is often desirable to slow the absorption of a drug from subcutaneous or intramuscular injection. The most common way to accomplish this is to inject a suspension of crystalline or amorphous material with poor water solubility. The rate of absorption of the drug becomes dependent on the rate of dissolution of the drug, which is, in turn, dependent on the physical state of the drug, for example, the crystal size and the crystalline form. Another approach to delaying absorption of a drug is to administer the drug as a solution or suspension in oil. Injectable depot forms can also be made by forming microcapsule matrices of drugs and biodegradable polymers, such as polylactide-polyglycolide. Depending on the ratio of drug to polymer and the composition of the polymer, the rate of drug release can be controlled. Examples of other biodegradable polymers include polyorthoesters and polyanhydrides. The depot injectables can also be made by entrapping the drug in liposomes or microemulsions, which are compatible with body tissues.

Suppositories for rectal administration of the drug can be prepared by mixing the drug with a suitable non-irritating excipient, such as cocoa butter and polyethylene glycol which are solid at ordinary temperature but liquid at the rectal temperature and will, therefore, melt in the rectum and release the drug.

Solid dosage forms for oral administration may include capsules, tablets, pills, powders, gelcaps and granules. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. Tablets and pills can additionally be prepared with enteric coatings and other release-controlling coatings.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferably, in a certain part of the intestinal tract, optionally in a delayed manner. Examples of embedding compositions which can be used include polymeric substances and waxes.

Dosage forms for topical or transdermal administration of a compound of this invention further include ointments, pastes, creams, lotions, gels, powders, solutions, sprays, inhalants or patches. Transdermal patches have the added advantage of providing controlled delivery of active compound to the body. Such dosage forms can be made by dissolving or dispersing the compound in the proper medium. Absorption enhancers can also be used to increase the flux of the compound across the skin. The rate can be controlled by either providing a rate controlling membrane or by dispersing the compound in a polymer matrix or gel. The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

In one embodiment, the therapeutic compound is delivered transdermally. The term "transdermal delivery" as used herein means administration of the pharmaceutical composition topically to the skin wherein the active ingredient or its pharmaceutically acceptable salts, will be percutaneously delivered in a therapeutically effective amount.

In some embodiments, the composition to be applied transdermally further comprises an absorption enhancer. The term "absorption enhancer" as used herein means a compound which enhances the percutaneous absorption of drugs. These substances are sometimes also referred to as skin-penetration enhancers, accelerants, adjuvants and sorption promoters. Various absorption enhancers are known to be useful in transdermal drug delivery. U.S. Pat. Nos. 5,230,897, 4,863,970, 4,722,941, and 4,931,283 disclose some representative absorption enhancers used in transdermal compositions and for topical administration. In some embodiments, the absorption enhancer is N-lauroyl sarcosine, sodium octyl sulfate, methyl laurate, isopropyl myristate, oleic acid, glyceryl oleate or sodium lauryl sulfoacetate, or a combination thereof. In some embodiments, the composition contains on a weight/volume (w/v) basis the absorption enhancer in an amount of about 1-20%, 1-15%, 1-10% or 1-5%. In some embodiments, to enhance further the ability of the therapeutic agent(s) to penetrate the skin or mucosa, the composition can also contain a surfactant, an azone-like compound, an alcohol, a fatty acid or ester, or an aliphatic thiol.

In one embodiment, the therapeutic compound is delivered via a transdermal patch.

In some embodiments, the transdermal composition can further comprise one or more additional excipients. Suitable excipients include without limitation solubilizers (e.g., $C_2$-$C_8$ alcohols), moisturizers or humectants (e.g., glycerol [glycerin], propylene glycol, amino acids and derivatives thereof, polyamino acids and derivatives thereof, and pyrrolidone carboxylic acids and salts and derivatives thereof), surfactants (e.g., sodium laureth sulfate and sorbitan monolaurate), emulsifiers (e.g., cetyl alcohol and stearyl alcohol), thickeners (e.g., methyl cellulose, ethyl cellulose, hydroxymethyl cellulose, hydroxypropyl cellulose, polyvinylpyrrolidone, polyvinyl alcohol and acrylic polymers), and formulation bases or carriers (e.g., polyethylene glycol as an ointment base). As a non-limiting example, the base or carrier of the composition can contain ethanol, propylene glycol and polyethylene glycol (e.g., PEG 300), and optionally an aqueous liquid (e.g., isotonic phosphate-buffered saline).

The method of the present invention employs the compounds identified herein for both in vitro and in vivo applications. For in vivo applications, the invention compounds can be incorporated into a pharmaceutically acceptable formulation for administration. Those of skill in the art can readily determine suitable dosage levels when the invention compounds are so used.

In accordance with a particular embodiment of the present invention, compositions comprising effective amounts of at least AGP and MLT (as described above), and a pharmaceutically acceptable carrier are contemplated.

Exemplary pharmaceutically acceptable carriers include carriers suitable for oral, intravenous, subcutaneous, intramuscular, intracutaneous, and the like administration. Administration in the form of creams, lotions, tablets, dispersible powders, granules, syrups, elixirs, sterile aqueous or non-aqueous solutions, suspensions or emulsions, and the like, is contemplated.

For the preparation of oral liquids, suitable carriers include emulsions, solutions, suspensions, syrups, and the like, optionally containing additives such as wetting agents, emulsifying and suspending agents, sweetening, flavoring and perfuming agents, and the like.

For the preparation of fluids for parenteral administration, suitable carriers include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized, for example, by filtration through a bacteria-retaining filter, by incorporating sterilizing agents into the compositions, by irradiating the compositions, or by heating the compositions. They can also be manufactured in the form of sterile water, or some other sterile injectable medium immediately before use. The active compound is admixed under sterile conditions with a pharmaceutically acceptable carrier and any needed preservatives or buffers as may be required.

The treatments may include various "unit doses." Unit dose is defined as containing a predetermined quantity of the therapeutic composition (a combination of AGP and MLT) calculated to produce the desired responses in association with its administration, e.g., the appropriate route and treatment regimen. The quantity to be administered, and the particular route and formulation, are within the skill of those in the clinical arts. Also of importance is the subject to be treated, in particular, the state of the subject and the protection desired. A unit dose need not be administered as a single injection but may comprise continuous infusion over a set period of time.

In some embodiments, pharmaceutical compositions of the present invention comprise effective amounts of AGP and MLT (and, optionally, additional agent(s)) dissolved or dispersed in a pharmaceutically acceptable carrier. The phrase "pharmaceutically or pharmacologically acceptable" refers to molecular entities and compositions that do not produce an adverse, allergic or other untoward reaction when administered to an animal, such as, for example, a human, as appropriate. The preparation of a pharmaceutical composition that contains at least AGP and MLT with, optionally, one or more additional active ingredient(s) will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity and general safety and purity standards as required by the FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The combination of AGP and MLT may comprise different types of carriers depending on whether it is to be administered in solid, liquid or aerosol form, and whether it needs to be sterile for such routes of administration as injection. The present invention can be administered intravenously, intradermally, transdermally, intrathecally, intraventricularly, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The combination of AGP and MLT may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle composition that includes a combination of AGP and MLT, one or more lipids, and an aqueous solvent. As used herein, the term "lipid" will be defined to include any of a broad range of substances that is characteristically insoluble in water and extractable with an organic solvent. This broad class of compounds is well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the combination of AGP and MLT may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic and/or prophylactic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% by weight of an active compound. In other embodiments, an active compound may comprise between about 2% to about 75% of the weight of the unit, or between about 25% to about 60% by weight, for example, and any range derivable therein. Naturally, the amount of active compound(s) in each therapeutically useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In some embodiments of the present invention, the combinations of AGP and MLT are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (see, e.g., U.S. Pat. Nos. 5,641,515; 5,580,579 and 5,792,451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup or elixir may contain the active compound sucrose as a sweetening agent, methyl and propylparabens as preservatives, a dye and/or flavoring, such as cherry or orange flavor. Of course, any material used in preparing any dosage unit form should be pharmaceutically pure and substantially non-toxic in the amounts employed. In addition, the active compounds may be incorporated into sustained-release preparations and formulations.

For oral administration the compositions of the present invention may alternatively be incorporated with one or more excipients in the form of a mouthwash, dentifrice, buccal tablet, oral spray, or sublingual orally administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically effective amount to a composition that may include water, binders, abrasives, flavoring agents, foaming agents, and humectants. Alternatively, the compositions may be fashioned into a tablet or solution form that may be placed under the tongue or otherwise dissolved in the mouth.

Additional formulations that are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

In further embodiments, the combination of AGP and MLT may be administered via a parenteral route. As used herein, the term "parenteral" includes routes that bypass the alimentary tract. Specifically, the pharmaceutical compositions disclosed herein may be administered for example, but not limited to intravenously, intradermally, transdermally, intramuscularly, intraarterially, intraventricularly, intrathecally, subcutaneous, or intraperitoneally. See, e.g., U.S. Pat. Nos. 6,753,514; 6,613,308; 5,466,468; 5,543,158; 5,641,515; and 5,399,363 (each specifically incorporated herein by reference in its entirety).

In some embodiments, the therapeutic compound is administered intrathecally. In some embodiments, the compound is administered intrathecally via an implantable pump. In one embodiment, the implantable pump comprises a SynchroMed™ II pump that stores and delivers medication into the intrathecal space (Medtronic).

Solutions of the active compounds as free base or pharmacologically acceptable salts may be prepared in water suitably mixed with a surfactant, such as hydroxypropyl cellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, dimethyl sulfoxide (DMSO), polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

In other embodiments, the combination of AGP and MLT may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidone and laurocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch." For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described, e.g., in U.S. Pat. Nos. 5,756,353 and 5,804,212 (each specifically incorporated herein by reference in its entirety). Likewise, the delivery of drugs using intranasal microparticle resins and lysophosphatidylglycerol compounds (U.S. Pat. No. 5,725,871, specifically incorporated herein by reference in its entirety) are also well-known in the pharmaceutical arts. Likewise, transmucosal drug delivery in the form of a polytetrafluoroethylene support matrix is described in U.S. Pat. No. 5,780,045 (specifically incorporated herein by reference in its entirety).

The term aerosol refers to a colloidal system of finely divided solid or liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

All publications herein are incorporated by reference to the same extent as if each individual publication or patent application was specifically and individually indicated to be incorporated by reference.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLES

Example 1: Synergistic Potential of Dual Andrographolide and Melatonin Targeting of Metastatic Colon Cancer Cells: Using the Chou-Talalay Combination Index Method The present example utilizes current analytic approaches to evaluate two mCRC cell lines (HT-29 and HCT-15) and colospheroids (HT-29-s and HCT-15-s) treated with combination therapy. Analysis has been applied for growth across a dose range, combination ratio, design layout, and computerized simulation of drug interaction using CompuSyn and Chou-Talalay's method.

This example demonstrates a step-by-step illustration for conducting drug combinations of andrographolide (AGP) and melatonin (MLT) in vitro using the CI method, and validation using an in vitro assay. We previously demonstrated the bicyclic diterpenoid AGP causes apoptotic CRC cell death associated with reactive oxygen species induction, angiogenic inhibition and tumor suppressor gene upregulation (Banerjee et al., Oncotarget, (2017), 8(16):26142-26153; Blanchard et al., Cell Physiol Biochem, (2018), 48(3):1259-1273). AGP can diminish 5-FU resistance (Islam et al., Cancer Lett, (2018), 420:129-145; Wang et al., Biochem Pharmacol, (2016) 121:8-17). Poor bioavailability, however, may hinder using AGP as a standalone therapy but does not rule out its use in combination therapies. Melatonin, a neuro-hormone (Banerjee et al., Life Sci, (2020), 255:117842; Reiter et al., Int J Mol Sci, (2017), 18(4):doi: 10.3390/ijms18040843), modulates dysregulation of various cancer signaling pathways (Favero et al., Front Pharmacol, (2018), 9:1086; Gil-Martin et al., 2019; Hao et al., J Exp Clin Cancer Res, (2019), 38(1):48). It is clinically safe at higher doses (Banerjee et al., Life Sci, (2020), 255:117842), can induce apoptosis, and increases sensitivity to chemotherapy in CRC (Asghari et al., Life Sci, (2018), 196:143-155; Iravani et al., J Gastrointest Cancer, (2019), 51(3): 748-75; Motilva et al., J Pineal Res, (2011), 51(1):44-60; Wu et al., Biomed Res Int, (2019), 2019:9740568). Accordingly, it inhibits CSCs by regulating the PrPc OCT4 axis (Lee et al., J Pineal Res, (2018), 65(4):e12519). This Example demonstrates that AGP and MLT combined (i) act with significant synergy (ii) provide a therapeutic impact on mCRC, colospheroids and 5-FU resistance cells viability (iii) mechanistically, induce ER stress and inhibit angiogenesis in vitro.

Materials and Methods

Cell Cultures

HT-29, HCT-15, and HCT-116 cells were generously provided by Dr. Lin Jiayuh at the University of Maryland School of Medicine and were grown in RPMI-1640 nutrient media with 10% FBS. All media were supplemented with a 1× solution of antimicrobial reagents (10,000 U/ml penicillin, 10,000 streptomycin, and 25 µg/ml amphotericin B) and 1× glutamine. Normal colon epithelial cells (FHC) were purchased from American Type Culture Collection (ATCC® CRL-1831)™ and grown as previously described (Banerjee et al., 2017).

Cell Cytotoxicity and Viability Assay

Cell cytotoxicity in the presence or absence of AGP and MLT was assessed using the MTT (Sigma Aldrich) assay as previously described (Banerjee et al., Helicobacter, (2016), 21(5):395-404). Cells ($1 \times 10^4$) were plated in phenol-free complete RPMI media and incubated at 37° C. under 5% $CO_2$ for 24 h. Cells were then simultaneously treated in quadruplicate wells with AGP (0-150 µM), MLT (0-3000 µM) or vehicle controls (0.1% DMSO). The media was replaced with MTT solution for each plate at its respective timepoint (either 24, 48, 72 h) followed by the addition of DMSO to dissolve the formazan crystals. Absorbance at 570 nM was determined using a microplate reader (Model 550, Bio-Rad, USA). The percent cell viability relative to the vehicle control was calculated using the following equation:

$$\% \text{ of Cell Viability} = 100 * \frac{\text{Absorbance Compound Treated} - \text{Absorbance media}}{\text{Absorbance Vehicle Treated} - \text{Absorbance Media}}$$

The IC50 value and slope (m) of the concentration-response curves were calculated using the CompuSyn software developed by Chou and Martin (Tun et al., Mar Drugs, (2019), 17(9): 10.3390/md17090536).

Colospheroid Formation Assay

HT-29 and HCT-15 cells were cultured in RPMI-1640 complete media as described earlier (Tsunekuni et al., Sci Rep, (2019), 9(1):14861). Cell cultures with 80% confluency were harvested with trypsin and gently pipetted to form a single cell suspension. After centrifugation, approximately 10,000 cells were plated on 6 well plates, coated with poly-L-lysine (0.01%) (EMD Millipore #A-005-C), in spheroid medium. The composition of spheroid medium is as follows: advanced DMEM:F12 (1×) reduced serum medium (1:1) (gibco, #12634-010, Gaithersburg, Md.), 1×penicillin/streptomycin, 1×L-glutamine (gibco, #25030-081), 1×N2 (Gemini #400-163), 1×B27 (Gemini #1 mM N-acetyl-L-cysteine (Sigma Aldrich, #A-7250), 10 ng/ml fibroblast growth factor (Gemini, #300-220P), 10 ng/ml epidermal growth factor (Gemini #300-803P), and Rock inhibitor (Y-27632 dihydrochloride; sigma; #Y0503), which at the concentration of 10 µM accelerates colospheroid formation. Colospheroids were formed at day 5 for HT-29 and day 3 for HCT-15 cells. For AGP and MLT treatment analysis, impact spheroids were permitted to grow for 5d (HT-29-s) and 3d (HCT-15-s). Spheroids viability was measured using the MTT assay as described in section 2.2.

5-FU Drug Resistance Cell Line

HT-29 and HCT-116 were used to develop 5-Fluorouracil, (5-FU; Sigma #F6627) drug resistant cell lines according to the published protocol (He et al. 2018). The 5-FU-resistant HT-29 and HCT-116 cells (HT-29R and HCT-116R) were treated with stepwise increasing concentrations of 5-FU (0, 25, 30, 35, 40, 45, 50 PM) over 11 months. Finally, the acquired drug-resistant cells were cultivated and stabilized in 10 µM 5-FU-containing RPMI complete medium.

Design Dose Range for AGP and MLT

To determine an upper bound on both the individual doses drugs, we measured maximum cell death (near 0% cell viability). AGP achieved this level at 150 µM and MLT at 3 mM for 48 h (Banerjee et al., Helicobacter, (2016), 21(5): 395-404, Reiter et al., Int J Mol Sci, (2017), 18(4), doi: 10.3390/ijms18040843). Because AGP is 20 times more potent than MLT, we conducted a 1:20 combination of AGP to MLT when testing their synergistic effect. Serial dilution was conducted up to 6 times to anchor the observed cell deaths along the dose range.

Determination of Combination Index with Simultaneous Treatment of AGP and MLT

To understand the Combination Index (CI), we first defined the fraction affected (Fa) and its counterpart, fraction unaffected (Fu). In our case, the percentage of viable cells determines the Fa, and 100—percentage of viable cells determines the Fu. The dose effect curve provides an overview of Fa vs. Dose (FIG. 2A and FIG. 2B). As expected, the individual AGP and MLT dose effect curves cradle the combinational dose effect curve below and above, respectively. This means that the total combinational dose to achieve the same Fa is greater than AGP's dose and less than MLT's dose. However, due to the 1:20 combinational ratio, we require less AGP and MLT absolutely. To further understand the relationship between Fa and dose, we evaluated the Median-Effect plot which displays $$\log\left(\frac{Fa}{Fu}\right) \text{ vs } \log(\text{Dose}).$$

The ratio between Fa and Fu aids in understanding when a given dose achieves the $IC_{50}$ value. At 50% cell viability, $$Fa = Fu \text{ where } \frac{Fa}{Fu} = 1. \text{ Therefore, } \log\left(\frac{Fa}{Fu}\right) = 0.$$

To linearly scale the datapoints, we also took the log of Dose. In this manner, the x intercept of the Median-Effect plot—also known as Dm—precisely determines the dose required to achieve the $IC_{50}$ value.

Immunoblotting

Immunoblotting was performed as previously described (Banerjee, Basu, et al. 2016). The primary antibodies used were against ATF6 (#MA5-16172; Thermo Fisher Scientific) phospho-PERK (Thr 981) (#sc-32577; Santa Cruz biotechnology), IRE-1 (#3294S; Cell Signaling), phospho-VEGFReceptor1/Flt-1 (Y1213) (#AF4170; R&D systems,), total VEGFReceptor1 (R&D systems, #AF321), FoxM1 (R&D systems, #AF3975), and GAPDH (#G8795; Sigma Aldrich). Blots were incubated with HRP-conjugated secondary antibodies followed by enhanced chemiluminescence (ECL) detection. Images were captured using a Syngene G Box digital imager (Frederick, Md.) and results were quantified with densitometry as previously described (Blanchard et al. 2018).

Quantitative Real-Time Polymerase Chain Reaction (qRT-PCR)

Gene expression was evaluated as previously described (Banerjee et al., Oncotarget, (2016), 7(27):41432-41444). Primer sequences are listed in Supplementary Table 1. Relative gene expression changes were calculated using the $2^{-\Delta\Delta CT}$ method, and expression normalization was accomplished using the housekeeping gene, GAPDH.

Statistical Significance

Statistical analysis was performed with Graph Pad Prism for Macintosh 5.0c (Graph Pad Software Inc., San Diego, Calif.). The mean S.E.M was calculated by one-way ANOVA. Significance between groups was analyzed using the post hoc Tukey's test and Bonferroni test. P values were considered significant if they were less than 0.05 and are indicated throughout using asterisks: *=P<0.05, =P<0.01, *P<0.001.

Results

AGP Synergizes with MLT and is More Potent than MLT in CRC Cells

It was necessary to establish the potency and slope of the concentration-response curves of AGP and MLT before determining the potential synergistic activity of these drugs. The MTT assay revealed a significant decrease in HT-29 and HCT-15 CRC cell viability in a time and dose dependent manner for both drugs (FIG. 1). The $IC_{50}$ value of AGP was determined to be 30 µM in both cell lines at 24 h (FIGS. 1A and D), which is consistent with the $IC_{50}$ value at 48 h. The $IC_{50}$ value of MLT was determined to be 1 mM at 48 h for both the HT-29 and HCT-15 cells (FIGS. 1B and E). The $IC_{50}$ values of AGP and MLT when used in combination were 9.3 µM and 0.18 mM, respectively (FIGS. 1C and F). However, there was a transient increase in the cell number with MLT treatment for HT-29, HCT-15 at 24 h. This increased number is also found in AGP and MLT combination treatment at 24 h. This may be due to the number of dividing cells in different cycles.

We then performed analytics to determine whether AGP acted synergistically with MLT. To test for synergy, we validated the MTT data using CompuSyn software. The constant ratio combination allows the computerized simulation of the dose-effect curves (FIGS. 2A and 2E), Median effect plots (FIGS. 2B and 2F), CI plots (FIGS. 2C and 2G), and Isobolograms (FIGS. 2D and 2H). FIGS. 2A and 2E show the concentration-dependent cytotoxicity of the individual and combinational drugs for HT-29 and HCT-15. In this case, we used a 1:20 ratio (150 µM AGP and 3000 µM MLT). The Dm (an indicator of the potency of the drug) of AGP in HT-29 and HCT-15 was 25.61 µM and 26.53 µM respectively, whereas the Dm of MLT was 1004 µM and 683.41 µM respectively, derived from the Median effect plots (FIGS. 2B and 2F). AGP and MLT achieved a Dm value of 125.732 for HT-29 and a Dm value of 107.127 µM for HCT-15 at 48h. Using the $IC_{50}$ values, we then determined whether the interaction between AGP and MLT would be classified as synergistic (CI<1), additive (CI=1), or antagonistic (CI>1). CI is defined by Chou and Talalay as the sum of the ratios between each drug's combinational dose and individual dose to achieve a specific Fa. In our case, we derived CI=0.35293 for HT-29 48 h and CI=0.34152 for HCT-15 48h with Fa=0.5. FIGS. 2C and 2G represent the remainder of the CI vs. Fa datapoints for HT-29 and HCT-15. The curve follows an exponential decay pattern. This demonstrates strong synergistic behavior between AGP and MLT. Additionally, the isobologram plot further demonstrates the shift in the combination of AGP and MLT doses to reach Fa=0.5, 0.75, and 0.9 (FIG. 2D and FIG. 2H). Evaluating the slopes of these graphs allows us to determine how changing the dose for one drug affects the other in order to maintain the Fa. Their relatively flat slopes (slopes near 0) indicate that a small increase in the AGP dose results in a large decrease in the dose of MLT. All curves and doses were calculated using CompuSyn. Overall, the combinational index analysis for AGP and MLT displays strong synergistic behavior for both HT-29 and HCT-15 at 48 h.

TABLE 1

| | | CI values for HT-29 | CI values for HCT-15 | Dm values for HT-29 | Dm values for HCT-15 |
|---|---|---|---|---|---|
| Dose Strategy | IC$_{50}$ values | | | | |
| AGP (µM) | 30 | — | — | 25.61 | 26.53 |
| MLT (1 mM) | 1 | — | — | 1004 | 683.41 |
| AGP + MLT | 9.3 + 0.18 | 0.35293 | 0.34152 | 125.732 | 107.127 |

IC$_{50}$ and CI values for AGP (0-150 µM) and MLT (0-3 mM) single dose or in combination in HT-29 and HCT-15 cells for 48 h.

Based on the 1:20 dilution of AGP and MLT, the AGP dose is approximately 6 µM and 5.1 µM and the MLT dose is 119.7 µM and 102 µM in HT-29 cells and HCT-15 cells, respectively. However, the hand-derived CI values and CompuSyn CI values were nearly the same, confirming that AGP and MLT have a synergistic effect. The results indicate that the IC$_{50}$ (Dm) value of AGP and MLT significantly decreased by ~5-6 fold and ~6-10-fold in comparison with the single dose for HCT-15 and HT-29 cells, respectively. In addition, the exponential decay curve shows the potency of AGP, which is 40-fold and 26-fold more than MLT in HT-29 and HCT-15 cells, respectively (FIGS. 2A and 2E).

AGP and MLT Synergism Combination Inhibits Colospheroids Viability

We extended our observations to the colospheroids model using HT-29-s and HCT-15-s treated with either AGP, MLT, or AGP and MLT in combination. Colospheroids were treated with increasing concentrations of AGP (0-37 µM) and MLT (0-0.75 mM) for 48 h (based on the previous experiment, FIG. 1). Dose dependent colospheroids death was confirmed by the MTT assay (FIG. 3A) and there was quantifiable dose-dependent deterioration (FIG. 3B). The IC$_{50}$ value of the combination group (AGP=9.3 µM and MLT=0.18 mM) was consistent with the treated colospheroids (FIG. 3A) and nonspheroids at 48 h (HT-29 and HCT-15 cells; FIG. 1C and FIG. 1F). The morphology of the colospheroids was evaluated by light microscopy. The number and size of spheroids significantly decreased with the increased concentration of AGP and MLT in the combined treatment in comparison with the untreated or single dose treatment (FIGS. 3C and D). To evaluate the inhibitory properties of the combined treatment, we selected HT-29-s for a clonogenic assay and conducted direct enumeration of the stained colonies (FIG. 3E). The treatment of colospheroids for 48 h resulted in significantly fewer colonies compared with the untreated and single treatments. Additionally, the number of colonies was found to be decreased with the increased concentration of the combined treatment (FIG. 3F).

AGP and MLT in Combination Synergistically Enhance 5-FU-CRC Cell Inhibition but not on Normal Colon Epithelial Cells Previous studies using in vitro models demonstrated that 5-FU significantly inhibits CRC cell proliferation (Zhang et al., Molecules, (2008), 13(8):1551-69). The limitation of overall response of 5-FU in advanced CRC is only about 10% and the combination of 5-FU with other anti-cancer drugs has merely improved the response rates (40-50%) (Douillard et al., Lancet 355, (2000), (9209):1041-7; Giacchetti et al., J Clin Oncol, (2000), 18(1):136-47). To determine if there is a synergistic impact of AGP and MLT when treating 5-FU lab-derived drug resistance cells (HT-29R and HCT-116R cells), an MTT assay was used to determine cell viability. The cytotoxic effect of combination treatments with different doses and time points are depicted in FIGS. 4A and 4B. The results demonstrate that the IC$_{50}$ values for the combination of AGP and MLT in HT29R were 9.3 µM of AGP and 0.18 mM of MLT at 48 h, which are consistent with the results from previous experiments (FIG. 4A). Additionally, the IC$_{50}$ values for the combination of AGP and MLT in HCT-116R were 18 µM and 0.37 mM respectively at 72 h (FIG. 4B). Treatment of normal colon epithelial cells with the IC$_{50}$ dose had little effect on cell numbers, which only dropped to approximately 80% (FIG. 4C).

AGP and MLT Synergistically Enhanced ER Stress Associated with Cell Death.

In previous studies, we have shown that AGP alone (45 µM) causes apoptotic CRC cell death through UPR mediated ER stress (Banerjee et al., Oncotarget, (2016), 7(27):41432-41444). To monitor if AGP and MLT synergistically causes CRC cell death through the ER stress, HT-29 and HCT-15 cells were treated with AGP (9.3 µM) and MLT (0.18 mM) alone or in combination for 48 h and were examined for ER stress inducers (IRE-1, ATF6 and PERK) expression. IRE-1 mRNA (FIG. 5A, P<0.05) and ATF6 (FIG. 5B, P<0.001) were increased by ~4-fold compared to the untreated HT-29 and HCT-15. Significant CHOP mRNA expression (FIG. 5C; P<0.001) was observed in the single treatment of AGP and in the combined treatment for both cell lines compared with the untreated cells. To determine the functional activity ER stress markers in 5-FU treated CRC cells, HT-29 and HCT-15 cells were treated with the IC$_{50}$ dose (13 µM in HT-29 and ~5 µM in HCT-15 respectively) of 5-FU as described in previous studies (Lim et al. 2007) for 48 h and 72 h respectively. 5-FU induced significant IRE-1 (p<0.001; HT-29, HCT-15) and ATF6 (HCT-15) mRNA expression, but attenuated CHOP mRNA expression (FIG. 5C). To see if the transcriptional level is reflected with the translational level, protein expression of ER stress markers was analyzed. As shown in FIGS. 5D, E, and F, IRE-1 and phospho PERK (FIG. 5I, 5J) were significantly elevated in the combinational treatment group for at least one cell lysate (HT-29) but ATF6 was significantly elevated in both HT-29 and HCT-15 (FIGS. 5G and H; p<0.001) cell lysates. No significant changes were found in the 5-FU treatment group except for the IRE-1 protein level in HT-29 cell lysates.

AGP and MLT Synergistically Impact on Angiogenic Inhibition

Earlier, we have shown that AGP alone reduced angiogenic signal (Blanchard et al., Cell Physiol Biochem, (2018), 48(3):1259-1273) in vitro and in vivo with a higher concentration. To investigate the impact of synergism, mCRC cells were treated and untreated as described above and the level of transcriptional and transitional angiogenic markers was evaluated. The AGP and MLT combined treatment group showed significant reduced levels of mVEGF165 (FIG. 6A), and mVEGF189 (FIG. 6B) in both cell lines compared to the untreated group. However, these transcript levels were increased in the 5-FU treatment group. The VEGF receptors transcript level was also monitored by qRT-PCR, as angiogenic signals through its receptor. A significantly decreased level of P-VEGF receptor1 (FIG. 6C; P<0.001) was observed in the combinational group in comparison to the untreated group. No significant change of mRNA levels was found in VEGF Receptor2 (data not shown). As expected, AGP and MLT synergistically reduced the expression of downstream angiogenic signal molecules, FoxM1, and PTTG1 mRNA levels. There was no more significant reduction found in the transcriptional level of FoxM1 and PTTG1 in 5-FU treated cells. The transcript level of FoxM1 and VEGF receptor was evaluated by the translational level using western blot. Greater reduction of protein for FoxM1 (FIG. 6F 1s' blot, FIGS. 6G-H) and phospho—VEGF receptor1 (FIG. 6F 2<sup>nd</sup> and 3<sup>rd</sup> blot and FIG. 6I-J) was found in the combinational group compared with the untreated and single compound groups. No further reduction of protein level was found in the 5-FU treated group. These results indicate that angiogenic signaling molecules is inhibited by dual treatment of AGP and MLT, and that this might be a cause of its synergistic effect.

DISCUSSION

Colorectal cancer statistics from 2020, indicate that the burden of CRC is shifting to younger individuals as incidence increases in young adults and declines in older age groups (Connell et al., Curr Treat Options Oncol, (2017), 18(4):23; Mauri et al., Mol Oncol, (2019), 13(2):109-131; American Cancer Society, Survival Rates for Colorectal Cancer, 2020). The disease is often metastatic in young CRC patients due to delayed diagnosis (Venugopal and Stoffel 2019). Despite advances in modem medical technology, CRC patients still face high mortality rates and poor prognosis (Zarour et al., Cell Mol Gastroenterol Hepatol, (2017), 3(2):163-173). Although the mainstay of CRC chemotherapy treatment is 5-FU, resistance to 5-FU is one of the major reasons for poor prognosis (Liu et al., Mol Cell Biochem, (2018), 449:(1-2):285-294). In addition, there are limited therapies at present to inhibit the colospheroids formation. Therefore, additional treatment regimens are needed to inhibit colospheroids formation and overcome drug resistance. The present study aimed to investigate the synergistic antiproliferative effects of AGP and MLT on mCRC in vitro. Andrographolide (AGP) is a lactone, (bicyclic diterpenoid) derived from *Andrographis paniculata* (Chen et al., *Anticancer Drugs*, (2014), 25(9):983-91; Islam et al., *Cancer Lett*, (2018), 420:129-145). It acts as an anti-inflammatory, immunomodulator, antioxidant and anticancer drug (Gao et al., *Cell Death Dis*, (2019), 10 (12):957; Tan et al., *Biochem Pharmacol*, (2017), 139:71-81; Lai et al., *J Immunol Res*, (2017), 7807313; Banerjee, A., *International Journal*, (2017), 2(2):1-2; Islam et al., Cancer Lett, (2018), 420:129-145; Khole et al., *Free Radic Biol Med*, (2019), 130:397-407; Li et al., J Cell Physiol, (2018), 234 (1):561-571; Banerjee et al., *Helicobacter*, (2016), 21(5): 395-404; Mussard et al., Antioxidants (Basel), (2019), 8(12); Rajagopal et al., *J Exp Ther Oncol*, (2003), 3(3):147-58; Soo et al., *Drug Discov Today* 24 (9):1890-1898; Yuwen et al., *Anticancer Drugs*, (2017), 28 (9):967-976; Zhang et al., *Oncol Lett*, (2017), 14(4):4305-4310; Zhou et al., *Biochem Pharmacol*, (2010), 79(9):1242-50). Several clinical trials demonstrate the positive effects of AGP on infectious disease and autoimmune disorders (Blanchard et al., *Cancers (Basel)*, (2019), 11(2), doi: 10.3390/cancers11020199). In vitro analysis demonstrates that AGP acts on cancer cells via apoptosis, anti-angiogenesis, autophagy and dysregulation of signaling pathway (Tan et al., *Biochem Pharmacol*, (2017), 139:71-81; Zhou et al., Biochem Pharmacol, (2010), 79(9):1242-50; Blanchard et al., *Cell Physiol Biochem*, (2018), 48(3):1259-1273; Kajal et al., Sci Rep, (2019), 9 (1):4073; Loh et al., *Cancers* (Basel), (2020), 12(2), doi: 10.3390/cancers12020387; Chen et al., *Carcinogenesis*, (2012), 33(11):2190-8; Peng et al., *J Exp Clin Cancer Res*, (2018), 37(1):248; Zhou et al., *Autophagy*, (2012), 8(3):338-49; Liu et al., *J Cell Physiol*, (2019), 234(6):9631-9639). Despite its efficacy, poor bioavailability may hinder the use of AGP as a stand-alone cancer therapy.

Melatonin is a neuro-hormone that upholds circadian rhythm and orchestrates many physiologic changes (Reiter et al., Cell Mol Life Sci, (2020), doi: 10.1007/s00018-019-03438-1; Sato et al., *J Pineal Res*, (2020), e12639). It modulates dysregulation of various cancer signaling pathways, is involved in regulation of immune function and tumor microenvironments, and acts as an antioxidative agent (Favero et al., Front Pharmacol, (2018), 9:1086; Hao et al., *J Exp Clin Cancer Res*, (2019), 38(1):48; Reiter et al., Int J Mol Sci, (2017), 18(4), doi: 10.3390/ijms18040843; Ganguly et al., *Free Radic Biol Med*, (2006), 41(6):911-25; Moradkhani et al., *J Cell Physiol*, (2020), 235:(2):745-757). Melatonin can induce apoptosis, increase sensitivity to chemotherapy and radiotherapy, and limit cellular proliferation, migration, and invasion in CRC (Asghari et al., *Life Sci*, (2018), 196:143-155; Iravani et al., J Gastrointest Cancer, (2019), 51(3):748-753; Motilva et al., J Pineal Res, (2011), 51(1):44-60; Wu et al., Biomed Res Int, (2019), 2019: 9740568). In addition, MLT enhances chemotherapeutic-induced cytotoxicity and apoptosis in several tumor cells and could be potentially applied to cancer treatment as a powerful synergistic agent (Pariente et al., *Cancer Chemother Pharmacol*, (2017), 80(5):985-998; Pariente et al., *Mol Cell Biochem*, (2018), 440(1-2):43-51; Pariente et al., *J Pineal Res*, (2016), 60(1):55-64). There is no published work on the combination of AGP and MLT resulting in disease. To reduce the concentration of AGP used as a monotherapy in our earlier studies and to better understand the molecular mechanism of AGP and MLT in combination on colon cancer cell death, we used AGP and MLT. In addition, to monitor the synergistic impact on young colon cancer, we used at least one young colon cancer cell line (HT-29) in the present study.

The therapeutic outcome of drug combination treatment depends on the regimen, dosage or drug ratios, and mode of action of the compounds. For some classes of compounds, certain ratios and schedules of administration are synergistic and others are antagonistic (Tun et al., *Mar Drugs*, (2019), 17(9): 10.3390/md17090536). The fixed 1:20 ratio in our results indicate that AGP synergizes with MLT at the concentration of approximately 9.3 µM of AGP and 180 µM (0.18 mM) of MLT. An important aspect of combinational therapy is to reduce cell toxicity and to increase efficacy of the compounds. Our published results demonstrate that AGP kills a panel of metastatic CRC cells with minimum toxicological effects on normal human cell lines and normal mouse colon organoids (Banerjee et al., *Helicobacter*, (2016), 21(5):395-404). We reported an IC50 value for AGP as a single therapy is 45 µM at 48 h. In the present example, to reduce the dose concentration, we combined AGP with MLT as MLT is very safe in CRC in vitro and in vivo studies, even at higher doses (Banerjee et al. 2020, Favero et al. 2018, Reiter et al. 2017, Reiter et al. 2020). Dose response studies reported herein indicate that AGP and MLT suppress the growth of monolayer HT-29 and HCT-15 cell cultures, colospheroids and 5-FU drug resistance cell culture significantly at lower doses of 9.3 µM and 0.18 mM, respectively. The IC50 dose is ~4.5 times lower than for AGP alone and ~10 times lower than for MLT alone.

Colospheroids are highly enriched in CRC cells (20-30%) (Yeung et al. 2010), and display cancer stem cell-associated features including drug resistance (Bakhshinyan et al. 2018, Kozovska, Gabrisova, and Kucerova 2014). The present study shows that AGP and MLT in combination reduce clonogenic properties, suggesting that these agents deplete colospheroid populations in the cancer cells. Therefore, the combination of these compounds would have added benefits and show the additive and synergistic effect at the indicated time point, thus offering potential for the treatment of mCRC, including young, adult CRC cell lines (HT-29 and HCT-15 respectively).

In our previous study, we demonstrated that AGP causes UPR mediated ER stress primarily through activation of IRE-1. In this study, we illustrate that the same mechanism is involved when AGP combined with MLT. We found that the combinatorial treatment could enhance the anti-cancer activity by triggering the ER stress-dependent apoptotic pathway, not only through the involvement of IRE-1 but also other ER transducers: ATF6, PERK and CHOP. Here, to best of our knowledge, this is the first report that indicates that AGP synergizes the anticancer effect of MLT in human cancer cells and demonstrates the underlying mechanisms of action. The mechanism by which AGP and MLT promote ER stress in cancer cells however is not clear. Therefore, further investigation on AGP and MLT synergism will be necessary to delineate its molecular interactions in cells and how these interactions induce ER stress.

To examine the mechanism of anticancer action of AGP and MLT further we tested the pathways associated with angiogenesis in single and combination drug treatment. In our previous study, we demonstrated that AGP alone (45 μM) suppresses angiogenic signaling (Blanchard et al, *Cancers (Basel)*, (2019), 11(2), doi: 10.3390/cancers11020199). It was of particular interest that the combination of AGP, reduced the expression of transcriptional and translational molecules (VEGF165, VEGF189, VEGF receptor1, FoxM1, PTTG1) involved in the angiogenic pathway more significantly compared with the untreated and single compound. This suggests that AGP and MLT collectively inhibit the expression of target proteins involved in angiogenesis. The mechanism by which AGP and MLT synergism influences the suppression of angiogenic signaling is not clear. Therefore, further investigation on AGP and MLT will be necessary to define its molecular interactions with VEGFR and other key elements in the angiogenic pathway.

The overall response rate to 5-FU, a first line agent for CRC, in adjuvant treatment is less than 15%. Additional efforts have been made to combine 5-FU with second line agents, such as cisplatin, interferon, leucovorin, methotrexate, N-phosphonoacetyl-L-asparatate (PALA) and uridine. However, results have not been satisfactory (Lim et al., *World J Gastroenterol*, (2007), 13(13):1947-52). Moreover, several studies have demonstrated that AGP enhances the 5-FU-induced antitumor effect and reverses 5-FU resistance in colon cancer through the c-MET pathway. Melatonin has also been demonstrated to increase the sensitivity of colon cancer cells to 5-FU treatment, as well as inhibit the growth of 5-FU resistant colorectal cancer cells through the upregulation of miR-215-5p and a downregulation of TYMS. In the present study, it is noteworthy that AGP and MLT combination inhibits angiogenic signals compared with 5-FU. This result strengthens the rationale regarding the use of AGP and MLT as a combined therapeutic agent for CRC treatment.

Several studies on the effects of AGP and MLT individually have been published (Asghari et al., *Life Sci*, (2018), 196:143-155; Banerjee et al., *Helicobacter*, (2016), 21(5): 395-404; Blanchard et al., *Cancers (Basel)*, (2019), 11(2), doi: 10.3390/cancers11020199; Iravani et al., *J Gastrointest Cancer*, (2019), 51(3):748-753; Khan et al., *Nutr Cancer*, (2018), 70(5):787-803; Motilva et al., *J Pineal Res*, (2011), 51(1):44-60; Wu et al., Biomed Res Int, (2019), 2019: 9740568). Their combinatorial effect, however, has not been explored. To our knowledge, this is the first report on the synergistic cytotoxicity of AGP and MLT in mCRC cell lines and this synergistic effect is validated with colospheroids and the drug resistance cell viability assay. The mechanism impacts the UPR signaling pathways by upregulating the ER stress transducers and causes angiogenic inhibition which leads to CRC cell death (FIG. 7).

Example 2: Impact of Andrographolide and Melatonin Combinatorial Drug Therapy on Metastatic Colon Cancer Cells and Organoids Methods Generation and Propagation of Patient-Derived Organoid Cell Cultures (PDOD)

Organoid cells were generated from stage 3 metastatic cancer tissue and cultured as previously described (Blanchard et al., *Cell Physiol Biochem*, (2018), 48(3):1259-1273; Banerjee et al., *Gastroenterology and Hepatology International Journal*, (2017), 2(2):1-2; Blanchard et al., *Cancers (Basel)*, (2019), 11(2)). The cultures were passaged when the aggregates reached a diameter of approximately 800 μm. Organoids were treated with 15 μM AGP, 0.5 mM MLT, or both for 48 h. Treated and untreated organoids were subjected to morphological analysis and immunofluorescence for Ki67 expression.

Cell Culture and Drug Treatment

T84, and Colo 205 colon cancer cell lines were cultured as previously published (Banerjee et al., *Oncotarget*, (2016), 7(27):41432-41444; Banerjee et al., *Oncotarget*, (2017), 8(16):26142-26153; Blanchard et al., *Cell Physiol Biochem*, (2018), 48(3):1259-1273; Blanchard et al., *Cancers (Basel)*, (2019), 11(2)). HT-29, and DLD-1 were grown in RPMI-1640 nutrient media in a humidified incubator at 37° C. with 5% $CO_2$. All media were supplemented with a 1× solution of antimicrobial reagents (10,000 U/ml penicillin, 10,000 streptomycin, and 25 pg/ml amphotericin B), 1× glutamine and 10% FBS. Mouse normal epithelial cells (GSM06) and prostate epithelial cells (RWPE1) cells were grown and cultured as previously described (Blanchard et al., *Cancers (Basel)*, (2019), 11(2)). When cell was grown 80% confluent, media was replaced with media containing 2% FBS with AGP (Sigma Aldrich, St. Louis, Mo.) and MLT (a kind gift from Professor Russel J. Reiter) with indicated dose and time point. Stock AGP (100 mM) and MLT (1 M) were prepared in DMSO and control wells received DMSO at a final concentration of 0.01%.

Cytotoxicity Assay

Cytotoxicity assay in the presence or absence of AGP or, MLT was assessed using the MTT assay as previously described (Banerjee et al., *Oncotarget*, (2016), 7(27):41432-41444).

Clonogenic Assay

HT-29 and DLD-1 cells were seeded in 6-well plates (approximately 50, 0000/well). The clonogenic assay was performed as previously described (Banerjee et al., Oncotarget, (2016), 7(27):41432-41444).

Quantitative Real-Time Polymerase Chain Reaction (qRT-PCR)

Gene expression was evaluated as previously described (Banerjee et al., *Oncotarget*, (2016), 7(27):41432-414440. Primer sequences are listed in Table 2. Relative gene expression changes were calculated using the $2^{-\Delta\Delta CT}$ method and expression normalization was accomplished using the housekeeping gene, GAPDH.

TABLE 2

| qRT-PCR primers | | |
|---|---|---|
| Gene | Primer sequence forward | Primer sequence reverse |
| GAPDH | 5'-CGACCACTTTGTCAAGCTCA-3'<br>SEQ ID NO: 1 | 5'-AGGGGAGATTCAGTGTGGTG-3'<br>SEQ ID NO: 2 |
| IRE-1 | 5'-GGGAAATACTCTACCAGCCT-3'<br>SEQ ID NO: 3 | 5'-GAAATCTCTCCAGCATCTTG-3'<br>SEQ ID NO: 4 |
| ATF6 | 5'-TCAGGGAGTGAGCTACAAGT-3'<br>SEQ ID NO: 5 | 5'-CTTGTGGTCTTGTTATGGGT-3'<br>SEQ ID NO: 6 |
| CHOP | 5'-TTCTCTGGCTTGGCTGACTG-3'<br>SEQ ID NO: 7 | 5'-CTGCGTATGTGGGATTGAGG-3'<br>SEQ ID NO: 8 |
| Bcl-2 | 5'-GGAGGCTGGGATGCCTTT3'<br>SEQ ID NO: 9 | 5'-ACCCATGGCGGTGACCATGC-3'<br>SEQ ID NO: 10 |
| Bax | 5'-GAGAGGTCTTTTTCCGAGTGG-3'<br>SEQ ID NO: 11 | 5'-CCTTGAGCACCAGTTTGCTG-3'<br>SEQ ID NO: 12 |
| XBP1 | 5'-AACCAGGAGTTAAGACAGCGCTT-3'<br>SEQ ID NO: 13 | 5'-CTGCACCCTCTGCGGACT-3'<br>SEQ ID NO: 14 |

Immunoblotting

Immunoblotting was performed as previously described (Banerjee et al., *Helicobacter*, (2016), 21(5):395-404). The primary antibodies used were against Cleaved caspase-3 (#MAB835) from R&D Systems, Caspase 3 (#9662), IRE-1(#3294) from Cell Signaling, Cyclin B1(GNS1, #sc-245), p-PERK (#sc-32577), PRX (A-6) (#sc-137150P), TRX (#sc-271281) from Santa Cruz Biotechnology, ATF-6 (#MA5-16172) from Thermo Fisher Scientific, melatonin receptor 1B or MT2 (#NLS9320 from Novus Biologicals and GAPDH (G8795) from Sigma Aldrich. Blots were incubated with HRP-conjugated secondary antibodies followed by enhanced chemiluminescence (ECL) detection. All secondary antibodies were purchased from KPL, Gaithersburg, Md. Images were captured using a Syngene G Box digital imager (Frederick, Md., USA) and results were quantified by densitometry as previously described (Blanchard et al., *Cancers (Basel)*, (2019), 11(2)).

Immunofluorescence

Patient derived organoids were grown in 1:1 mixture of Matrigel and advanced DMEM:F12 (Life Technologies) supplemented with 1× penicillin/streptomycin, 1x glutamine, 1×N2, 1×B27, 1 mM N-acetyl-L-cysteine, 20 ng/ml fibroblast growth factor and 50 ng/ml epidermal growth factor at 37° C. on a 4-chambered glass slide. Fully grown organoids were treated with or without AGP and MLT for 48 h. whole mount staining was carried out as previously described with slight modifications (Blanchard et al., *Cell Physiol Biochem*, (2018), 48(3):1259-1273; Wiener et al., *Proc Natl Acad Sci USA*, (2014), 111(21):E2229-2236). After desired time of treatment organoids were washed three times with 1×PBS and fixed with 4% paraformaldehyde at room temperature for 30 min, permeabilized with 0.2% Triton X-100 for 20 min, blocked with 2.5% horse serum (Vector; S-2012) and incubated with 1:40 dilution of Ki-67 (M-19) (#sc-7846) at 4° C. for overnight. After incubation organoids were washed 3 times with PBS (10 mins/wash) and incubated with Alexa Flour 488 labeled donkey anti-goat IgG (H+L) (1:200) (ab 150129).

Fluorescence Microscopy and Image Acquisition

Fluorescence microscopy and colony counting were performed using an inverted fluorescence microscope (Olympus IX-71, Pennsylvania, USA). Images for patient derived organoids (PDOD) were taken at 400× magnification. Fluorescence intensity was quantified using ImageJ software version 1.39 (NIH). RGB composite images from control and treated groups were created using Axion Vision rel, 4.6 and analyzed. Images from five different fields were used for statistical analysis as previously described (Banerjee et al., *Oncotarget*, (2017), 8(16):26142-26153; Blanchard et al., *Cell Physiol Biochem*, (2018), 48(3):1259-1273; Wiener et al., *Proc Natl Acad Sci USA*, (2014), 111(21):E2229-2236).

Statistical Analysis

Statistical analysis was performed with Graph Pad Prism for Macintosh 5.0c (Graph Pad Software Inc., San Diego, Calif.). The mean S.E. was calculated by one-way ANOVA. Significance between groups was analyzed using the post hoc Tukey's test and Bonferroni test. A $p < 0.05$ was considered statistically significant.

Results

Co-Treatment with AGP and MLT Inhibits Cell Viability

Previous study have demonstrated that the $IC_{50}$ value of AGP for T84 and Colo 205 is 45 μM, whereas $IC_{50}$ value of MLT for CRC range from 1-2.5 mM (Banerjee et al., Oncotarget, (2016), 7(27):41432-41444; Garcia-Navarro et al., *J Pineal Res*, (2007), 43(2):195-205; Liu et al., *Mol Med Rep*, (2017), 16(6):9383-9392). To reduce the AGP concentration, T84, Colo 205, HT-29 and DLD-1 cells were co-treated with AGP (0-150 μM) and MLT (0.5 mM) for 24, 48 and 72 h to assess the effect on cell proliferation. MTT assays revealed co-treatment significantly reduced cell viability in a time and dose dependent manner (FIG. 8A-D). The $IC_{50}$ was determined to be 15 μM for AGP and 0.5 mM for MLT at 48 h. This concentration was used for subsequent assays. Additional experiments were performed to determine the efficacy of this co-treatment on normal cells such as gastric surface mucous cell lines from transgenic mice GSM06 and normal prostate epithelial cells (RWPE-1). Co-treatment of normal epithelial cells with the same concentration of AGP and MLT had little effect on cell numbers (FIG. 8E-F). These data suggest that AGP and MLT co-treatment selectively inhibits CRC cells but not normal cells. The inhibitory properties of AGP and MLT on HT-29 and DLD-1 cells were also determined in a clonogenic assay and direct enumeration of stained colonies (FIG. 9). Co-treatment of cells for 48 h resulted in significantly fewer colonies compared with the untreated cells. Co-treatment significantly decreased the number of colonies (P<0.001) by 48 h.

Co-Treatment with AGP and MLT Induces Apoptosis and Apoptosis Signaling is Dependent Upon ER Stress

Earlier studies showed that AGP, at a concentration of 45 µM, causes apoptotic CRC cell death due to the unfolded protein response (UPR) mediated ER stress pathway (Banerjee et al., *Oncotarget*, (2016), 7(27):41432-41444; Banerjee et al., *Oncotarget*, (2017), 8(16):26142-26153; Blanchard et al., *Cell Physiol Biochem*, (2018), 48(3):1259-1273). To verify the function of a lower concentration of AGP on CRC cells, T84 and Colo 205 cells were co-treated with AGP and MLT as indicated. As shown in FIGS. 10A and 3B, co-treatment significantly increased the 17 kDa cleaved Caspase 3 levels (P<0.001) as compared with the control and treatment with either AGP or MLT alone. The ratio of cleaved caspase 3 and total caspase 3 also significantly increased (FIG. 10C; P<0.001). Additionally, co-treatment significantly upregulated pro-apoptotic BAX mRNA expression (FIG. 10D; P<0.001), but not mRNA of Bcl-2 (FIG. 10E T84). To verify the apoptotic induction with co-treatment of AGP and MLT is due to the UPR, T84 and Colo 205 mRNA levels were monitored for UPR signaling pathway initiators IRE-1, ATF-6 and PERK. Co-treatment resulted in a significant increase in IRE-1 and ATF-6 mRNA expression (~4.5-6-fold, P<0.001) at 48 h (FIG. 11A, B). Consistent with IRE-1 activation, an increase in XBP-1 mRNA expression of over 3.5-fold for T84 and 1.5-fold for Colo 205 was observed at 48 h (FIG. 11C; P<0.001 and P<0.05). Expression of CHOP, which can be activated by XBP-1, was also significantly increased (FIG. 11D; P<0.05 for T84 and P<0.01 for Colo 205). An additional experiment was performed to monitor the ER stress protein level (IRE-1, p-PERK, and ATF-6) by western blot. ER stress protein analysis revealed increases only in IRE-1 in T84 and Colo 205 co-treated groups and ATF-6 expression in T84 co-treated group (FIGS. 11E, F, and H). Taken together, the results indicate that co-treatment induced apoptosis is mediated via ER stress and the IRE-1 activation pathway.

Co-Treatment Induced G2/M Cell Cycle Arrest and Involvement of ROS Molecules.

AGP alone suppresses Cyclin B1 expression in T84 and Colo 205 cell lysates (Banerjee et al., *Oncotarget*, (2017), 8(16):26142-26153). To monitor the Cyclin B1 expression in co-treatment groups, T84 and Colo 205 cells were treated with or without AGP and MLT. The cell lysates were analyzed for Cyclin B1 expression. FIGS. 12A and 12A1 show AGP and MLT could effectively suppress Cyclin B1 expression (P<0.001) as compared to untreated control and AGP or MLT alone groups. Next, we monitored antioxidant protein expression (Prx, and Trx) by western blot. Peroxiredoxin (Prx) and Thioredoxin-1 (Trx-1) are upregulated in many human cancers, including colon and rectum, and in some cancers, downregulation of Prx promotes apoptosis (Kim et al., *Free Radic Biol Med*, (2016), 91:264-274; Lin et al., *Cancer Lett*, (2017), 401:1-10; Raffel et al., *J Lab Clin Med*, (2003), 142(1):46-51).

Our findings indicate co-treatment significantly downregulates Prx and Trx expression (FIG. 12B-B1; P<0.05-P<0.001) in both cell lysates. Taken together, the results depicted that co-treatment causes cell cycle arrest through downregulation of cyclin B1 and Prx- and Trx-mediated oxidative stress-induced cell apoptosis.

Impact of AGP and MLT on Patient Derived Organoids

Patient derived organoids were generated as previously described (Blanchard et al., *Cell Physiol Biochem*, (2018), 48(3):1259-1273) (FIG. 13A). Matured organoids were treated with or without AGP (15 µM) and MLT (0.5 mM) for 48 h. A loss of membrane integrity was found in the co-treatment group as compared with the AGP or MLT alone groups. Untreated group retained the structure of 3D organoids with intact membrane integrity (FIG. 13B). Immunofluorescence staining for Ki-67 expression was evaluated to measure the effect of AGP, MLT or co-treatment of AGP and MLT on organoids growth. Ki-67 was greatly reduced in all treatment groups as compared to the untreated group; maximum reduction was found in the co-treatment group (FIG. 13C).

Discussion

Colorectal cancer is the third most prevalent malignant tumor worldwide and the number of new cases may increase to nearly 2.5 million in 2035[27,28]. The 5-year survival rate for CRC is ~64%, but drops to 12% for metastatic CRC, and therefore, additional treatment regimens are needed to develop effective approaches for medical intervention[29].

Previous studies have demonstrated that AGP alone causes inhibition of CRC cell proliferation in metastatic cell lines, and patient derived organoids at a concentration of 45 µM. The inhibition was shown to be due to ER stress mediated apoptosis (Banerjee et al., *Oncotarget*, (2016), 7(27):41432-41444; Banerjee et al., *Oncotarget*, (2017), 8(16):26142-26153; Blanchard et al., *Cell Physiol Biochem*, (2018), 48(3):1259-1273). Moreover, AGP displayed synergistic effect with chemotherapeutic drugs in CRC cells and hepatocellular carcinoma cells (Khan et al., *Endocr Metab Immune Disord Drug Targets*, (2020), 20(6):930-942; Yang et al., *Cancer Lett*, (2009), 276(2):180-188). In vitro and in vivo studies have demonstrated the significant role AGP can have in re-sensitizing 5-Fu-resistant HCT116 (HCT116/5-FuR) cells to the cytotoxic effects of 5-Fu. AGP reverses 5-Fu resistance in human CRC through increasing the expression of BAX[11]. AGP, either alone or in combination with cisplatin, also induces CRC apoptotic cell death via increasing the expression of BAX and Bcl-2 and increasing the association of Fas and FasL (Lin et al., *Toxicol Sci*, (2014), 139(1):108-120). Additional study provided the evidence its possible clinical application for enhancing the antitumor effort (Su et al., *Drug Des Devel Ther*, (2017), 11:3333-3341). Recently, it is reported the synergistic cytotoxicity of AGP and MLT in mCRC cell lines, colospheroids and 5-FU drug resistance cells and the molecular mechanism is apoptosis due to unfolded protein response mediated ER stress and angiogenic inhibition (Banerjee et al., *Eur J Pharmacol*, (2021), 897:173919). In the present study, we have used a combination of AGP and MLT for metastatic CRC cell inhibition as both compounds have anti-angiogenic, apoptotic, cell cycle arrest dysregulation of various cancer signaling pathways and involved in regulation of immune function and tumor microenvironments (Banerjee et al., *Eur J Pharmacol*, (2021), 897:173919). Here, we examined the uses of a lower concentration of AGP when administered in combination with MLT (0.5 mM). The therapeutic concentration of MLT (0.5 mM) was selected because it modulates several signaling pathways which are considered likely anti-metastasis, anti-proliferative, and pro-apoptotic pathways in cancer cells (Hao et al., *J Exp Clin Cancer Res*, (2019), 38(1):48; Lee et al., *J Pineal Res*, (2018), 65(4):e12519; Liu et al., *Mol Med Rep*, (2017), 16(6):9383-9392; Reiter et al., *Int J Mol Sci*, (2017), 18(4); Reiter et al., *Cell Mol Life Sci*, (2020). Moreover, MLT does not show undesired side effects, even at extremely high doses (Banerjee et al., *Life Sci*, (2020), 255:117842; Fic et al., *Int J Mol Sci*, (2017), 18(7)). However, on pharmacological grounds, MLT can be designated as a synergistic or potentiating effect and it may have a potential clinical implication in the treatment of several pathologies including neurodegenerative diseases (Romero et al., *J Pineal Res*, (2010), 49(2):141-148). Additionally, it inhibits CRC stem cells by regulating the PrP$^c$-Oct4 axis. A synergistic effect has also been observed with MLT when combined with 5-Fu by inhibiting the stem cell markers Oct4, Nanog, Sox2 and ALDH1A1 through regulation of PrP$^c$ (Lee et al., *J Pineal Res*, (2018), 65(4):e12519).

We screened the potential effect of an AGP and MLT co-treatment on a panel of CRC cells and normal cells. The $IC_{50}$ value of AGP in co-treatment is reduced 3-fold compared with AGP alone (Banerjee et al., *Oncotarget*, (2016), 7(27):41432-41444; Banerjee et al., *Oncotarget*, (2017), 8(16):26142-26153). Co-treatment of AGP and MLT inhibits cell viability and has significantly less cytotoxicity in mouse normal epithelial cells and human prostate epithelial cells. Co-treatment induces an increase in mRNA and protein levels of IRE-1, one of the three major ER stress activated UPR proteins; an observation that is consistent between two cell lines. Increases in transcription of ATF6 mRNA were observed in T84 and Colo 205 cells, but protein levels only increased in T84 cell lysates at 48 h. Therefore, involvement of UPR protein at 48 h is associated with an increase in pro-apoptotic signaling and cell death.

Reactive oxygen species (ROS) generation can induce carcinogenesis by stimulating mutation and can inhibit tumor progression by inducing apoptotic signals (Majumder et al., *J Biochem Mol Toxicol*, (2020), DOI: 10.1002/jbt.22643). Studies have demonstrated the importance of ROS in AGP-induced anti-cancer cell activities (Banerjee et al., *Oncotarget*, (2017), 8(16):26142-26153). Among the Prx family of proteins, Prx-1 is the most prominent subtype with an increase in expression in tumor tissues (Kim et al., *Cancer Res*, (2007), 67(2):546-554). Trx-1, a small redox protein, also has shown an increase in expression when observed in many human cancers including colon cancer. We have observed that co-treatment downregulates Prx-1 and Trx expression, which is consistent with the elevated expression of cleaved caspase 3, CHOP, and XBP-1 and the decreased expression of Cyclin B1.

Patient derived models are necessary to improve knowledge about CRC and to develop new therapeutic approaches. Our model represents an informative system employing both in vitro and ex vivo testing, support by a previous study (Grassi et al., *Cell Death Dis*, (2019), 10(3):201). Our data show the impact of AGP and MLT on the inhibition of organoid morphology derived from third metastatic CRC patient tissue, which corroborates the inhibition of Ki67. A significant amount of Ki67 in organoids in the untreated group is consistent with another study which reports elevated Ki67 in CD133$^+$, CD44$^+$/CD24$^-$ and ALDH$^+$ CSCs (Li et al., *PLoS One*, (2014), 9(2):e87264). Multiple studies have demonstrated that besides having a role in cell proliferation, Ki67 is also involved in metastasis and invasion of cancer cells (Li et al., *PLoS One*, (2014), 9(2):e87264; Cidado et al., *Oncotarget*, (2016), 7(5):6281-6293). These studies support a role for dual therapy using the natural products AGP and MLT against CRC.

The dual treatment was demonstrated to inhibit cell viability and promote cell cycle arrest as well as promote ER stress dependent apoptosis signaling in CRC cell lines. Cancer organoids derived from metastatic CRC were also shown to display membrane disruption and reduced proliferative activity in response to AGP and MLT treatment compared to control organoids.

---

What is claimed is:

1. A method of treating cancer in a subject, comprising administering to the subject an effective amount of a combination of andrographolide and melatonin, wherein the combination of andrographolide and melatonin acts synergistically to treat cancer, wherein the cancer is metastatic colorectal cancer.

2. The method of claim 1, wherein the subject is a human subject.

3. The method of claim 1, wherein the cancer is young-onset colorectal cancer.

4. The method of any of claim 1, wherein the cancer in the subject comprises at least one solid tumor.

5. The method of claim 1, wherein the cancer is resistant to one or more chemotherapeutic agents.

6. The method of claim 5, wherein the chemotherapeutic agent is fluorouracil.

7. The method of claim 1, wherein the treatment inhibits the proliferation of cancer stem cells.

8. The method of claim 1, wherein the treatment inhibits colospheroid viability.

9. The method of claim 1, wherein the treatment induces endoplasmic reticulum stress in cancer cells.

10. The method of claim 1, wherein the treatment inhibits angiogenesis.

11. The method of claim 1, wherein the treatment promotes apoptosis of cancer cells.

12. The method of claim 1, wherein andrographolide is administered in an amount of about 500 mg to about 3000 mg and melatonin is administered in an amount of about 1000 mg to about 6000 mg.

13. The method of claim 1, wherein andrographolide is administered in an amount of about 0.05 g to about 5 g, and melatonin is administered in an amount of about 0.25 g to about 10 g.

14. The method of claim 1, wherein andrographolide is administered in an amount of about 1 mg/kg body weight of the subject to about 20 mg/kg body weight of the subject and melatonin is administered in an amount of about 10 mg/kg body weight of the subject to about 250 mg/kg body weight of the subject.

15. The method of claim 1, wherein a weight ratio of andrographolide to melatonin that is administered is in a range of from about 1:1 to about 1:20.

16. The method of claim 1, wherein a weight ratio of andrographolide to melatonin that is administered is in a range of from about 1:10 to about 1:15.

17. The method of claim 1, wherein andrographolide and melatonin are administered orally.

18. The method of claim 17, wherein andrographolide and melatonin are formulated in the form of a capsule, a tablet, a pill, a powder, a gel cap, or granules.

19. The method of claim 18, wherein andrographolide and melatonin are formulated in the form of a controlled release capsule, tablet, or pill.

20. A composition for treating cancer in a subject, comprising an effective amount of a combination of andrographolide and melatonin wherein the combination of andrographolide and melatonin acts synergistically to treat cancer, wherein the cancer is metastatic colorectal cancer.

21. The composition of claim 20, further comprising a pharmaceutically acceptable carrier.

22. The composition of claim 21, wherein a weight ratio of andrographolide to melatonin is in a range of from about 1:1 to about 1:30.

* * * * *

SEQUENCE LISTING

<160> NUMBER OF SEQ ID NOS: 14

<210> SEQ ID NO 1
<211> LENGTH: 20
<212> TYPE: DNA
<213> ORGANISM: Artificial sequence
<220> FEATURE:
<223> OTHER INFORMATION: primer

<400> SEQUENCE: 1
cgaccacttt gtcaagctca                                          20

<210> SEQ ID NO 2
<211> LENGTH: 20
<212> TYPE: DNA
<213> ORGANISM: Artificial sequence
<220> FEATURE:
<223> OTHER INFORMATION: primer

<400> SEQUENCE: 2
aggggagatt cagtgtggtg                                          20

<210> SEQ ID NO 3
<211> LENGTH: 20
<212> TYPE: DNA
<213> ORGANISM: Artificial sequence
<220> FEATURE:
<223> OTHER INFORMATION: primer

<400> SEQUENCE: 3
gggaaatact ctaccagcct                                          20

```
<210> SEQ ID NO 4
<211> LENGTH: 20
<212> TYPE: DNA
<213> ORGANISM: Artificial sequence
<220> FEATURE:
<223> OTHER INFORMATION: primer

<400> SEQUENCE: 4
gaaatctctc cagcatcttg                                                   20

<210> SEQ ID NO 5
<211> LENGTH: 20
<212> TYPE: DNA
<213> ORGANISM: Artificial sequence
<220> FEATURE:
<223> OTHER INFORMATION: primer

<400> SEQUENCE: 5
tcagggagtg agctacaagt                                                   20

<210> SEQ ID NO 6
<211> LENGTH: 20
<212> TYPE: DNA
<213> ORGANISM: Artificial sequence
<220> FEATURE:
<223> OTHER INFORMATION: primer

<400> SEQUENCE: 6
cttgtggtct tgttatgggt                                                   20

<210> SEQ ID NO 7
<211> LENGTH: 20
<212> TYPE: DNA
<213> ORGANISM: Artificial sequence
<220> FEATURE:
<223> OTHER INFORMATION: primer

<400> SEQUENCE: 7
ttctctggct tggctgactg                                                   20

<210> SEQ ID NO 8
<211> LENGTH: 20
<212> TYPE: DNA
<213> ORGANISM: Artificial sequence
<220> FEATURE:
<223> OTHER INFORMATION: primer

<400> SEQUENCE: 8
ctgcgtatgt gggattgagg                                                   20

<210> SEQ ID NO 9
<211> LENGTH: 18
<212> TYPE: DNA
<213> ORGANISM: Artificial sequence
<220> FEATURE:
<223> OTHER INFORMATION: primer

<400> SEQUENCE: 9
ggaggctggg atgccttt                                                     18

<210> SEQ ID NO 10
<211> LENGTH: 20
<212> TYPE: DNA
<213> ORGANISM: Artificial sequence
<220> FEATURE:
```

-continued

```
<223> OTHER INFORMATION: primer

<400> SEQUENCE: 10
acccatggcg gtgaccatgc                                                   20

<210> SEQ ID NO 11
<211> LENGTH: 21
<212> TYPE: DNA
<213> ORGANISM: Artificial sequence
<220> FEATURE:
<223> OTHER INFORMATION: primer

<400> SEQUENCE: 11
gagaggtctt tttccgagtg g                                                 21

<210> SEQ ID NO 12
<211> LENGTH: 20
<212> TYPE: DNA
<213> ORGANISM: Artificial sequence
<220> FEATURE:
<223> OTHER INFORMATION: primer

<400> SEQUENCE: 12
ccttgagcac cagtttgctg                                                   20

<210> SEQ ID NO 13
<211> LENGTH: 23
<212> TYPE: DNA
<213> ORGANISM: Artificial sequence
<220> FEATURE:
<223> OTHER INFORMATION: primer

<400> SEQUENCE: 13
aaccaggagt taagacagcg ctt                                               23

<210> SEQ ID NO 14
<211> LENGTH: 18
<212> TYPE: DNA
<213> ORGANISM: Artificial sequence
<220> FEATURE:
<223> OTHER INFORMATION: primer

<400> SEQUENCE: 14
ctgcaccctc tgcggact                                                     18
```